United States Patent
Bristol

(10) Patent No.: US 7,324,949 B2
(45) Date of Patent: Jan. 29, 2008

(54) IMPLANTABLE MEDICAL DEVICE MANAGEMENT SYSTEM

(75) Inventor: Guy Scott Bristol, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1061 days.

(21) Appl. No.: 10/025,023

(22) Filed: Dec. 19, 2001

(65) Prior Publication Data

US 2002/0138155 A1 Sep. 26, 2002

Related U.S. Application Data

(60) Provisional application No. 60/278,821, filed on Mar. 26, 2001.

(51) Int. Cl.
*A61B 5/00* (2006.01)
(52) U.S. Cl. .............................. 705/3; 702/183; 604/65
(58) Field of Classification Search ................ 705/2–3; 702/183; 604/65
See application file for complete search history.

(56) References Cited

U.S. PATENT DOCUMENTS

| | | | | |
|---|---|---|---|---|
| 5,375,604 A | * | 12/1994 | Kelly et al. ................. | 600/484 |
| 5,544,661 A | * | 8/1996 | Davis et al. ................. | 600/513 |
| 5,781,442 A | * | 7/1998 | Engleson et al. ........... | 700/214 |
| 5,871,465 A | * | 2/1999 | Vasko ........................ | 604/65 |
| 5,895,371 A | * | 4/1999 | Levitas et al. .............. | 604/500 |
| 6,167,309 A | | 12/2000 | Lyden ........................ | 607/29 |
| 2005/0021297 A1 | * | 1/2005 | Hartlaub .................... | 702/183 |

OTHER PUBLICATIONS

St.Jude Medical Implants First Genesis System; Innovative Therapeutic Breakthrough for Treating CHF and AF; PR Newswire; New York:: Feb. 10, 2000; pp. 1-4.*
Hospitals signing up quickly for cardiac implant device for transplant candidates; Anonymous: Hospital Materials Management. Ann Arbor : Jan. 1999. vol. 24, Iss.1; p. 5; pp. 1-2.*
Medtronic brochure, "SynchroMed Infusion System", (1995).

* cited by examiner

*Primary Examiner*—Florian Zeender
*Assistant Examiner*—Vanel Frenel
(74) *Attorney, Agent, or Firm*—Mary P. Bauman; Mary Y. Redman

(57) ABSTRACT

A suite of applications is provided for the administration of implantable medical devices, particularly implantable therapeutic substance infusion devices. The applications may be accessed over a public network, such as the Internet, and may be run using middleware. The applications provide for the administration of medical devices as they pertain to a particular patient, the ordering of therapeutic agents from participating third-party dispensaries, the scheduling of device maintenance and explant events, and the review of literature and educational materials pertaining to a particular medical device or class of devices.

73 Claims, 18 Drawing Sheets

Fig. 2

| | |
|---|---|
| ADA | Application Development Architecture |
| ETA | Enterprise Technology Architecture |
| HIPPA | Health Insurance Patient Privacy Act |
| FDA | Food and Drug Administration |
| B2B | Business-to-Business |
| B2C | Business-to-Cosumer |
| CMS | Content Management System |
| PIN | Personal Identification Number (works like a password) |
| DRS | Device Registration System (Oracle® Instance) |
| JSP | Java Server Page |
| LDAP | Lightweight Directory Access Protocol (via Oblix® policy server) |
| SSL | Secure Socket Layer (Browser data communications encryption) |
| VPN | Virtual Private Network (IP-Server implementation, B2B data encryption) |
| XML | eXtensible Markup Language (for machine readable documents and B2B communications) |
| TSS | Therapy Support Services, or TSS for short |
| SAIT | Server Administrator Information Technology |
| SRS | System Requirements Specification |
| DD | Design Detail Document |
| SVP | System/Software Validation Plan |
| VT | Short for Verification Test checklist |
| SVR | System/Software Validation Report |

*Fig. 3*

⊕ Medtronic                Medtronic Therapy Support Services

Welcome! Please file out the following forms to register. Fields marked with an * are required.

*User ID:            [dchdd]
*Password:           [********]        *Confirm: [********]
Your password must be at least 7 characters in length and must contain at least 2 numeric characters.

Salutation:          [None ▶]
*First Name:         [Doc]                       Street Address: [9376 Birch Blvd.]
Preferred Name:      [          ]                City:           [St. Paul]
Middle Name:         [          ]                *State:         [MN]
*Last Name:          [Holiday]                   Zip:            [55122]
Name Suffix:         [M.D.]                      Phone Number:   [612-555-1234]
*E-Mail Address:     [holiday@domain.com]        Fax:            [            ]

*Are you a Physician?                            ⦿Yes ○No
*Do you want to receive informational e-mails?   ⦿Yes ○No Connection Type      [DSL or Cable Modem ▶]      Location           [Clinic ▶]
Computer Type        [Window's based PC ▶]       Number of Computers [2]

I understand that my User ID and password are for my use only and I agree that I will not share my login information with anyone, nor login using another's User ID.

[Submit to Medtronic]   [Clear and Start Over]

Fig. 4

Contact Medtronic

Email Us!

Please fill out the form below to receive more information about the Therapy Support Services.

Fields marked with * are required.

*First Name:
*Last Name:
*E-mail Address:
Street Address:
City:
*State:
Zip:
*Phone Number:
Fax:
*Message:

Issue: | Forget your Username/Password ▼ |

Fields marked with * are required.

[Send] [Clear]

Fig. 7

Medtronic

MEDTRONIC THERAPY SUPPORT SERVICES

User (authenticated)

Dashboard • Tour • Maintenance • Login • Logout

Medtronic
Pump Replacement Report

| Patient Name | Model | Implant Date | | -3-SD | Likely Date | +3-SD |
|---|---|---|---|---|---|---|
| Patient, John R. | 861718 | 12/31/1996 | Calculate | 30-Dec-1999 | 30-Jun-2001 | 30-Dec-2002 |
| Patient, John R. | 861718 | 06/14/1997 | Calculate | 14-Jun-2000 | 14-Dec-2001 | 14-Jun-2003 |
| Patient, John R. | 861718 | 06/20/1997 | Calculate | 20-Jun-2000 | 20-Dec-2001 | 20-Jun-2003 |
| Patient, John R. | 861718 | 06/30/1997 | Calculate | 30-Jun-2000 | 30-Dec-2001 | 30-Jun-2003 |
| Patient, John R. | 861718 | 07/22/1997 | Calculate | 22-Jul-2000 | 22-Jan-2002 | 22-Jul-2003 |
| Patient, John R. | 861718 | 07/25/1997 | Calculate | 25-Jul-2000 | 25-Jan-2202 | 25-Jul-2003 |
| Patient, John R. | 861718 | 08/19/1997 | Calculate | 19-Aug-2000 | 19-Feb-2002 | 19-Aug-2003 |
| Patient, John R. | 861718 | 08/19/1997 | Calculate | 19-Sep-2000 | 19-Mar-2002 | 19-Sep-2003 |
| Patient, John R. | 861718 | 11/03/1997 | Calculate | 03-Nov-2000 | 03-May-2002 | 03-Nov-2003 |
| Patient, John R. | 861718 | 12/11/1997 | Calculate | 11-Dec-2000 | 11-Jun-2002 | 11-Dec-2003 |
| Patient, John R. | 861718 | 03/06/1998 | Calculate | 06-Mar-2001 | 06-Sep-2002 | 06-Mar-2004 |
| Patient, John R. | 861718 | 03/18/1998 | Calculate | 18-Mar-2001 | 18-Sep-2002 | 18-Mar-2004 |

Repeat Interpretation 76

 Medtronic
MEDTRONIC THERAPY SUPPORT SERVICES

| | |
|---|---|
| Patient: | Patient, John R. |
| Pump Model | 861718 |
| Implant Date: | 08/05/1998 |
| Avg. Daily Infusion Volume: | .5 mL |

[ Calculate ]

| | |
|---|---|
| -3 SD: | 05-Nov-2001 |
| Mean Date: | 05-Mar-2002 [43.6 Months] |
| +3 SD | 05-Mar-2002 |

Important: This calculation assumes constant daily infusion volume over the life of the pump. To improve your calculation, enter your best estimate of the programmed average daily infusion volumes since implant.

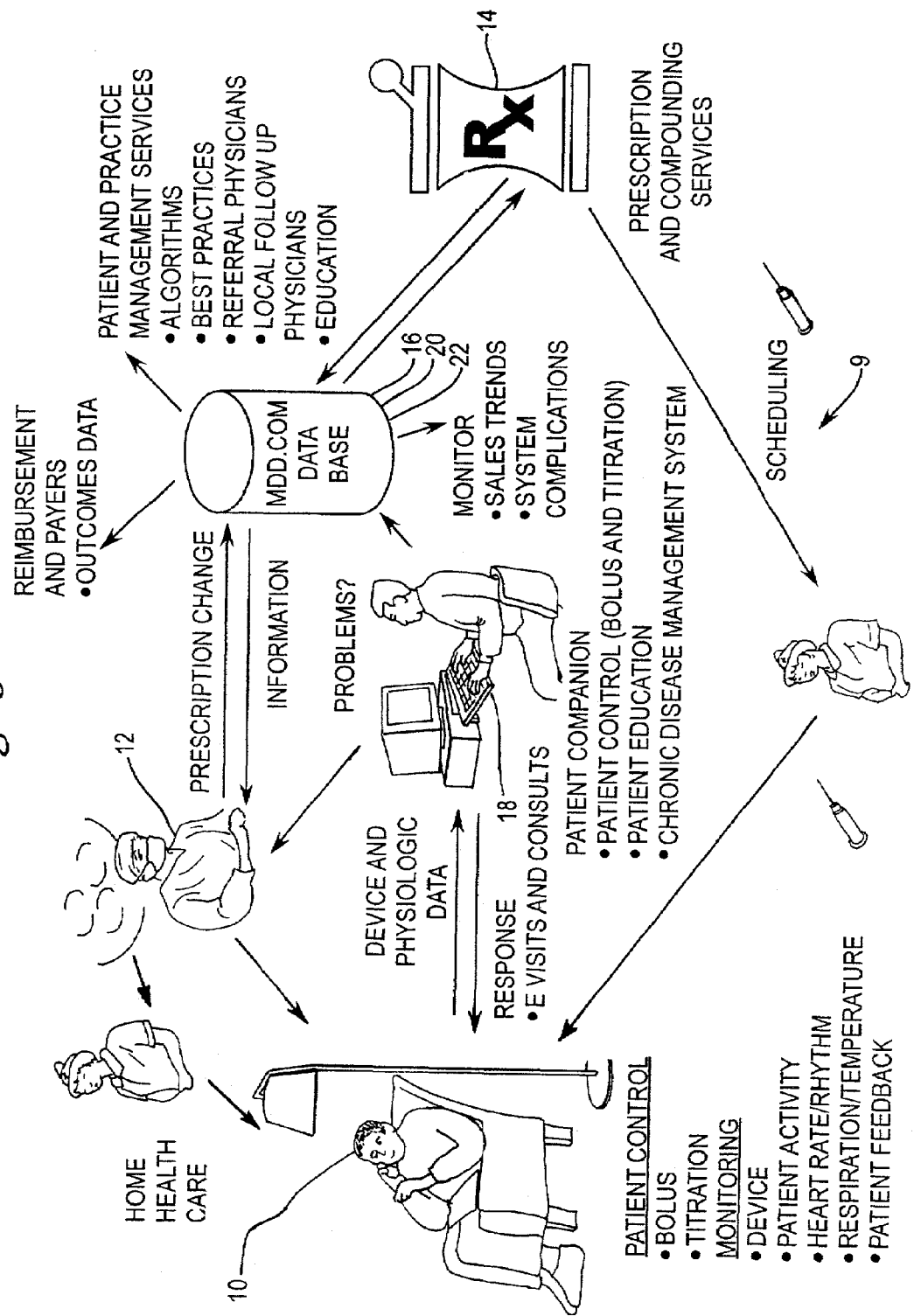

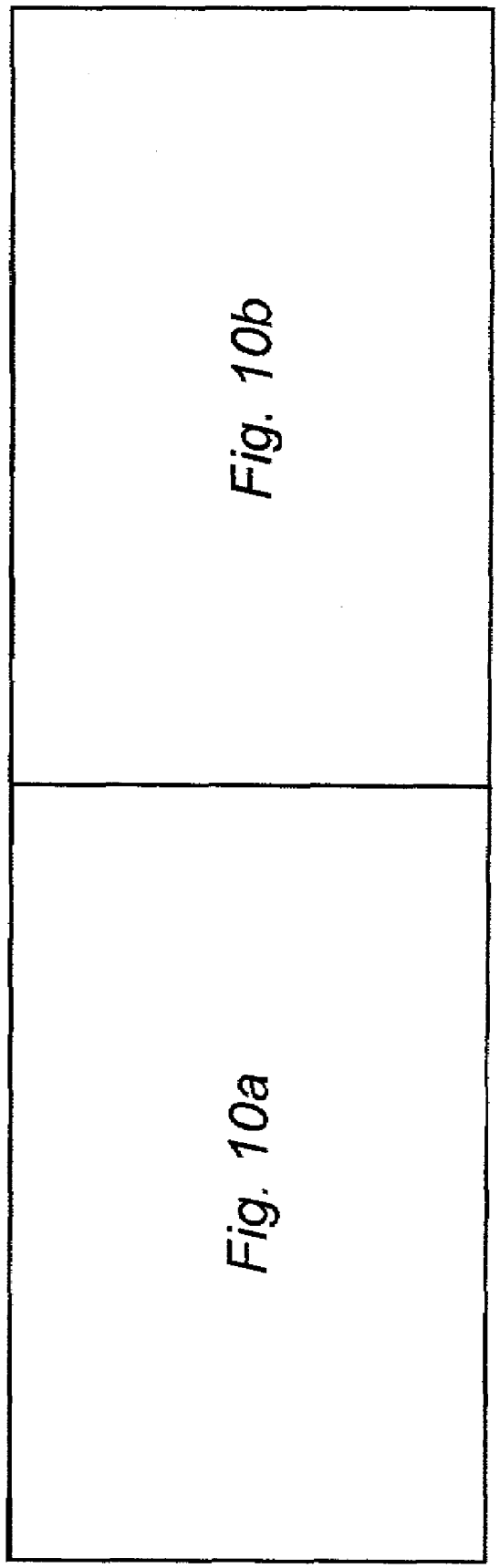

IMPLANTABLE MEDICAL DEVICE MANAGEMENT SYSTEM

CROSS-REFERENCE TO RELATED APPLICATIONS

This application claims the benefit of U.S. Provisional Application No. 60/278,821, filed Mar. 26, 2001, which is incorporated herein by reference in its entirety.

FIELD OF THE INVENTION

The present invention generally relates to an implantable therapeutic substance infusion device, also known as an implantable "drug pump". Specifically, the invention is a remote server providing configuration capabilities for implantable drug pumps. The server provides utilities to consider aspects of the implantable pump along with specific drug formulations. More specifically the invention relates to real-time communication between physicians and the implantable therapeutic substance infusion device to assist the clinician in managing patients receiving intrathecal therapy.

BACKGROUND OF THE INVENTION

Optimally, a technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide medical services in a manner independent of time and location.

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is an implantable therapeutic substance infusion device.

An implantable therapeutic substance infusion device is implanted by a clinician into a patient at a location appropriate for the therapy. Typically, a therapeutic substance infusion catheter is connected to the device outlet and implanted to infuse the therapeutic substance such as a drug or infusate at a programmed infusion rate and predetermined location to treat a condition such as pain, spasticity, cancer, and other medical conditions. Many therapeutic substance infusion devices are configured in such a way that the device can be replenished with therapeutic substance through a septum while the device is implanted, so the time the device can be implanted may not be limited by therapeutic substance capacity. An example of an implantable therapeutic substance infusion is shown in Medtronic, Inc. product brochure entitled "SynchroMed® Infusion System" (1995). The infusion device has a housing; a power source; a therapeutic substance reservoir configured for containing a therapeutic substance and being refilled with the therapeutic substance while implanted; a therapeutic substance pump fluidly coupled to the therapeutic substance reservoir, and electrically coupled to the power source; and, electronics electrically coupled to the power source and coupled to the therapeutic substance pump. The electronics include a processor; memory coupled to the processor; an infusion program residing in memory, the infusion program capable of being modified once the therapeutic substance infusion device is implanted; and, transceiver circuitry coupled to the processor for externally receiving and transmitting therapeutic substance infusion device information.

An implantable therapeutic substance delivery device, also known as a drug pump, can be used for a wide variety of therapies such as pain, spasticity, cancer, and many other medical conditions. An implantable therapeutic substance delivery device is typically implanted by a clinician, such as a surgeon, in a sterile surgical procedure performed under local, regional, or general anesthesia. The implantable therapeutic substance delivery device is generally implanted subcutaneously about 2.5 cm (1.0 inch) beneath the skin where there is sufficient subcutaneous tissue to support the implanted system. Once the therapeutic substance delivery device is implanted into the patient, the incision can be sutured closed and the therapeutic substance delivery device can begin operation.

The therapeutic substance delivery device operates to infuse a therapeutic substance at a programmed rate into a patient. The therapeutic substance is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance can be replenished in some embodiments of the implanted therapeutic substance delivery device by inserting a non-coring needle connected to a syringe filled with therapeutic substance through the patient's skin into a septum on the therapeutic substance delivery device to fill the implanted device reservoir. If the therapeutic substance delivery device requires replacement due to conditions such as battery depletion or other conditions, an incision is made near the implanted therapeutic substance delivery device, and the old therapeutic substance delivery device is removed, also known as explanted. After the old therapeutic substance delivery device has been explanted, typically a new therapeutic substance delivery device is then implanted.

Prior art methods of clinical intrathecal therapy are generally limited to the implantable therapeutic substance infusion device's physical requirements. For example, if a physician needs to review the performance parameters of an implantable therapeutic substance infusion device in a patient, it is likely that the patient will have to go to the clinic. Further, if the medical conditions of a patient with an implantable therapeutic substance infusion device warrant a continuous monitoring or adjustment of the device, the patient would have to stay in a hospital indefinitely. Such a continued treatment plan poses both economic and social problems.

Currently, there is very little direct connectivity between the patient, the implantable drug pump manufacturer, the physician, the pharmacist, and the implantable device surgeon with the implantable drug pump. For instance, when the clinician implants a drug pump into a patient, the patient really has no other involvement with the implanted drug pump. Typically the patient merely conveys to the clinician their responses to their therapy during periodic medical appointments. Likewise, the clinician, implantable drug pump manufacturer, and pharmacist have no coordination with each other.

Presently, the clinician will receive the medical device and a manual of operation and installation containing generalized listings to assist the clinician in planning how to use the drug pump with a drug therapy. The listings are based upon an average of drug pump parameters and likely real-life scenarios which are made quite conservative to avoid the risk of failure of the drug pump while installed inside the patient. Therefore, the only way for a clinician to get a better understanding of the technical characteristics of the drug pump is reading the drug pump manual or a possible discussion with a drug pump technical representative.

The pharmacist's coordination with other drug pump stakeholders is limited as well. The pharmacist typically will receive a drug pump medication prescription by fax, mail, or delivery; then fill the prescription and deliver the medication to the clinician. Therefore, no interaction occurs between the pharmacist, clinician, drug pump manufacturer, and patient. This is a very compartmentalized way of performing intrathecal therapy with minimal information interchanged. Thus the capabilities of the implantable drug pump and the capabilities of the therapeutic substances are not optimized.

Electrically powered implanted therapeutic substance infusion devices can require replacement once implanted due to factors such as battery consumption, corrosion damage, and mechanical wear. Since replacement of the implanted device requires an invasive procedure of explanting the existing device and implanting a new device, it is desirable to only replace the infusion device when replacement is required. Replacement of previous implantable infusion devices was typically scheduled based upon a worst-case statically forecasted elective replacement period. The worst-case scenario typically resulting in the implanted infusion device being replaced several months or even years before the implanted infusion device required replacement. Some previous implantable pulse generators such as pacemakers have monitored a single sensed battery condition to estimate replacement time for the implanted device or battery such as shown in U.S. Pat. No. 6,167,309 "Method For Monitoring End Of Life For Battery" by Lyden (Dec. 26, 2000).

For the foregoing reasons, it would be desireable, in connection with the implantation of therapeutic substance infusion devices to provide a system by which the lifespan of the device could be predicted, thus increasing the infusion device's effective life, reducing the need for a clinician to perform static longevity forecasts for therapy changes, facilitate a broader range of possible elective replacement scheduling for the convenience of the patient and clinician, and many other improvements.

Dosage calculators in some form are currently available for clinicians to use. However, because present dosage calculation systems do not provide the patients, other clinicians, pharmacists and dispensaries, and drug pump manufactures with connectivity to each other. These devices operate with a minimum of real-world information from these valuable sources of pertinent information. Further, prior art dosage calculators do not provide the ability to view a patient's drug history, and intrathecal drug history, and assess drug dosage trends or perform a convenient detailed check of a patient's information such as drug allergies. Finally, the prior art devices do not take into account the detailed specification of the implanted drug pump when therapeutic substance infusion therapy, such as intrathecal therapy, is being prepared. Currently the clinician may have some very broad parameters of the pump. For example, the clinician might have the implantable pump's drug reservoir volume, or they might know the ranges in which the infusion rates operate. However, such general parameters yield a prediction of dosage and device lifespan, which could be improved upon.

The proliferation of patents with implantable drug pumps worldwide has made it desirable to provide remote services to the drug pumps and timely clinical care to the patient. Frequent use of programmer devices to communicate with implantable medical devices and provide various remote services, consistent with co-assigned patents, titled "System and Method for Transferring Information Relating to an Implantable Medical Device to a Remote Location," U.S. Pat. No. 6,250,309; "Apparatus and Method for Remote Troubleshooting, Maintenance and Upgrade of Implantable Device Systems," U.S. Pat. No. 6,442,433; "Tactile Feedback for Indicating Validity of Communication Linik with an Implantable Medical Device," U.S. Pat. No. 6,644,321; "Apparatus and Method for Automated Invoicing of Medical Device Systems," U.S. Pat. No. 6,385,593; "Apparatus and Method for Remote Self-Identification of Components in Medical Device Systems," U.S. Pat. No. 6,754,538; "Apparatus and Method to Automate Remote Software Updates of Medical Device Systems," U.S. Pat. No. 6,363,282; "Method and Apparatus to Secure Data Transfer From Medical Device Systems," U.S. Pat. No. 7,039,810; "Implantable Medical Device Programming Apparatus Having An Auxiliary Component Storage Compartment," U.S. Pat. No. 6,411,851; "Remote Delivery Of Software-Based Training For Implantable Medical Device Systems," U.S. Pat. No. 6,386,882; "Apparatus and Method for Remote Therapy and Diagnosis in Medical Devices Via Interface Systems," U.S. Pat. No. 6,418,346; "Virtual Remote Monitor, Alert, Diagnostics and Programming For Implantable Medical Device Systems" U.S. Pat. No. 6,497,655; "Implantable Therapeutic Substance Infusion Device with Active Longevity Projection" U.S. Pat. No. 7,001,359; "Implantable Therapeutic Substance Infusion Device Configuration System," U.S. Pat. No. 7,072,725; all of which are hereby incorporated by reference herein in their entirety, has become an important aspect of patient care. Thus, in light of the disclosures herein, the present invention provides a vital system and method of dispensing/delivering efficient therapy and clinical care to the patient.

SUMMARY OF THE INVENTION

The present invention provides a suite of applications for support of implanted medical devices, particularly implantable therapeutic substance infusion devices, or "drug pumps". The invention may be configured to provide a single user login and authentication process for a central server hosting a suite of applications useful to practitioners, suppliers, and other parties with an interest in the operation of implantable medical devices. The present invention enables medical device manufacturers to define and market a unique suite of web tools for specific customer segments, while protecting a common "user experience" environment for a public server connected to a network, including a public network. The invention provides for efficient, integrated Internet software. Suites consist of applications that add value for the customer and are built around their medical practice workflows. Applications can be defined as "shared" or "dedicated" to a specific suite.

The suites will preferably include an Internet GUI Application Portal that will display the primary available applications provided to users by the system. Preferably, the GUI will be a user-configurable template. A first application in the suite is termed a "Specialty Pharmacy" application, which provides a communication between a physician and a pharmacy. This communication allows a physician to place orders or refills of a therapeutic agent on behalf of a patient with the pharmacy. The physician can also then change the prescription order if necessary. The application provides the physician with refill and prescription order reminders for the implantable drug pump. An automated dosage calculator is utilized in the application to provide predictive scenarios of contemplated treatment regimens for a patient. This dosage calculator can also insure that two or more non-compatible prescriptions are not prescribed at the same time and can issue a warning to the physician if a lethal dosage is prescribed.

A second application of the suite, according to the present invention, is called a "Device Registration System" ("DRS") lookup and update. This application provides for the management of implanted therapeutic substance infusion devices. It allows the user to register an implantable therapeutic substance infusion device with the device's manufacturer as well as provide feedback to the manufacturer regarding the operation of the implanted therapeutic substance device of the lifetime of the device. A user can access reports that detail a therapeutic substance infusion device's capabilities and interconnectivities with other devices.

A third application is labeled a "Pump Practice Management Support and Replacement Report" application. This will preferably provide for a "Pump Replacement Report" to estimate battery End-Of-Life for implanted pumps. The report is based on an algorithm provided by the device manufacturer. The report preferably provides minimum, maximum, and predicted failure dates. This feature allows the physician to contact the patient, e.g., through a communication network and schedule a replacement before the pump alarm is triggered.

A fourth application labeled "Therapy Specific Literature and Materials" operates as a server file or "web page" providing links to other files containing technical news, articles, and educational materials. Therefore the user can inform themselves about the devices they are working with as well as keeping up to date on the latest developments with devices, which are already implanted.

BRIEF DESCRIPTION OF THE DRAWINGS

FIG. 2 is a list of acronyms applicable to the present invention;

FIG. 3 is an embodiment of a new user registration page according to the present invention;

FIG. 4 is an embodiment of a LOGIN page according to the present invention;

FIG. 7 is an embodiment of the Pump Replacement Report according to the present invention;

FIG. 8 is an embodiment of the estimated pump lifecycle page according to the present invention;

FIG. 9 is a diagrammatic representation of a connectivity system according to the present invention;

DETAILED DESCRIPTION OF THE INVENTION

Figure 1:
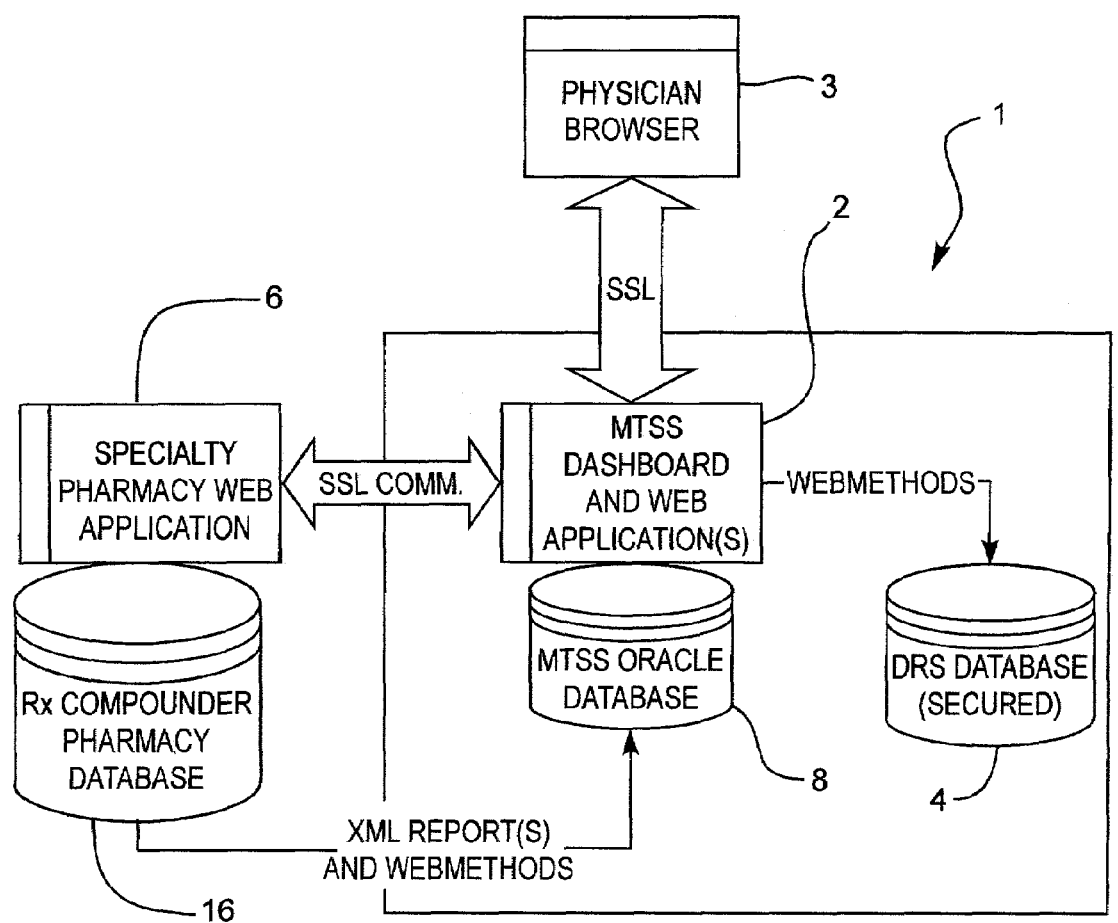
FIG. 1 is a conceptual component model of a preferred embodiment of the present invention.

To assist in an understanding of the invention, a preferred embodiment or embodiments will now be described in detail. Reference will be frequently taken to the figures, which are summarized above. Reference numerals will be used to indicate certain parts and locations in the figures. The same reference numerals will be used to indicate the same parts or locations throughout the figures unless otherwise indicated. The term application is frequently referred to below. It is to be understood that the term application can mean any general purpose programming language with a number of features, which make the language well suited for use on the World Wide Web (e.g., Java applets).

With respect to FIG. 1, a Conceptual Component Model 1 of a preferred embodiment of the present invention is depicted. A system according to the present invention preferably consists of multiple Business-to-Consumer (B2C) or Business-to Business (B2B) style applications (box 2), customized, as well as enhanced to provide unique functionality that will be convenient to clinicians and patients. Users of the system will typically be authenticated physicians, or healthcare professionals authorized by a physician (box 3). The present invention provides for single sign-in, registration, and user authentication; a customizable GUI interface, which may be browser enabled, to enable a physician or healthcare professional to access the system remotely. The system also provides for collection and storage of user identification, specialty, and profile. The system preferably allows a clinician/user to effect on-line prescription ordering, e.g. with a business partner of the administrator of the system or server. Users will also have access to a Device Registry System, which will be provided as a read-only database 4, in order to consider the specifications and registration information of various medical devices. The system will also implement real-time calculations for pump replacement report by model, according to information learned from the body of implanted devices existing in the patient population. Preferably, the system will also provide access to on-line clinical publications and education materials authored by, for example, a medical device manufacturer, or third parties, which may be of interest to users.

With reference to FIG. 2, a list of acronyms pertinent to the present invention is provided. The application data server may be implemented with one of various middleware access applications or environments as are known in the art. This present invention may be implemented as one of a suite of interactive business applications on a site administered by a central service provider. This provider may be, for example, a medical device manufacturer. Upon accessing the central server, e.g., using an Internet browser, the user is preferably prompted for authentication information. Unless the central server is accessed over a secure or dedicated line, this authentication information in turn is preferably not provided as plain text, as it would then be liable to eavesdropping. Rather, the authentication information may be provided using an encrypted virtual channel, such as the secure socket layer or https protocols.

With reference again to FIG. 1, the features of the present invention as regards application code and user interfaces may be implemented in any of various browser-based technologies, e.g. Java®/JSP (Java Sever Page) (with HTML). A middleware utility may be utilized for application data access to relational databases, the databases being maintained by the server administrator but made available to users. User and patient registration/profile and application data storage may similarly be implemented using a relational database, e.g., Oracle®. Preferably, the administrator of the system will take steps to implement security systems to protect access to the central server and databases, e.g., firewalls.

The user is provided with a front-end interface, which may be implemented as a static configuration of four interactive web applications running in a "thumbnail" or windowed mode. The interface may also be implemented as a Content Management System (CMS) top-level template designed to establish a collection (suite) of applications. This enables collections of web-based tools to market segments of customers to meet their specific needs, e.g. pain specialists. The applications specific to this system will be designed as plug-and-play installable components or utilities within the GUI (or CMS version of the interface).

A system according to the present invention preferably provides for administrative support and account maintenance, and will include a "Maintenance feature" for changing the data associated with the application. The maintenance screens will only be accessible to system administrators. Included in this feature will be that ability to add, update, or disable user entries. The ability to add or update entries in the lookup tables will also be included. User Registration, Authentication, and Security are affected as follows: "User registration" is preferably done in two parts. The first provides basic user identity information and lets them assign their own password. Users may be granted a security class suitable for allowing access to public information on the central administrator's server site, including a Preview Tour of functionality provided by the present invention. This level of access may, for example, enable personalization of the user's "home page" on the site, but will preferably not allow access to Internet Applications provided according to the present invention. The second registration process is to sign up for full access to the present invention via the Internet GUI. This requires user verification prior to upgrading the user privileges to a suitable security level, via the server administrator Maintenance screen.

The initial suite will include an Internet GUI Application Portal 2 that will preferably display the primary available applications provided to users by the system. Preferably, the GUI will be a user-configurable template. The Applications may be integrated into the GUI using Server-side or JSP "includes". Users may be provided with the ability to maintain their own addresses and non-secured user account information.

The first application in this suite may be termed a "Specialty Pharmacy" application 6. The actual operation of the Pharmacy may be implemented by the server administrator, or by a third party in a manner in which it is transparent to the server administrator. In this embodiment, the server administrator will preferably not in any way monitor the Pharmacy application or the data transmissions, thus ensuring Physician-Pharmacist privacy.

The second application of the suite, according to the present invention, may be termed a "Device Registration System" ("DRS") lookup and update. A lookup application is provided that may access DRS database 4 maintained by the server administrator, either directly or by using a set of stored procedures provided by the server administrator. A full-featured lookup and update application may also be provided using middleware applications to enable access to DRS database 4 through a series of adapters provided by the server administrator.

In the embodiment of the present invention in which the administered medical device is an implantable pump, the third application may be termed a "Pump Practice Management Support and Replacement Report" application. This will preferably provide for a "Pump Replacement Report" to estimate battery End-Of-Life for implanted pumps. The report will be based on an algorithm provided by the device manufacturer. The report will preferably provide minimum, maximum, and predicted failure dates. This feature will allow the physician to contact the patient, e.g., through a communication network or via POTS, and schedule a replacement before the pump alarm is triggered.

Another embodiment of the present invention provides an application, which may be termed "Therapy Specific Literature and Materials". This application may be implemented as a simple server file or "web page" by providing links to other files containing technical news, articles, and educational materials. The invention will preferably provide for the ability of the user to order special reprints from independent publishers. These items will preferably be targeted at the user's areas of interest.

Preferably, at least three security classes for Internet users of the instant invention will be provided. The users of this system will include: Registered (identified) users without full access to the invention (Class B); Physicians and their proxies (Class C); and Patients and their proxies (Class B or C) depending upon application. System administrators of the server system implementing the invention may be given a Class D designation, after special authorization and training.

The authentication function of the present application may be implemented in, for example, an Oblix/LDAP (Lightweight Directory Access Protocol) solution. The invention will also preferably provide a graphical "tour" (application walkthrough) of the GUI to demonstrate features. The registration process may be implemented in two-parts, e.g. Class B users may be granted access to a tour, while Class C users, for example, may be granted further access to the functionality of the invention. The registration process preferably collects information about users, and may enable physical authentication.

A certain number of users, e.g., 35 to 100 users, may be given access as "Specialty Pharmacy" users, through user ID's granted by the server administrator. The Specialty Pharmacy user access control may be implemented, for example, as a pharmacy access code or Personal Identification Number (PIN).

The pharmacy users will have access to the applications of the invention as described above. All data exchanges with the pharmacy vendor will preferably be accomplished using common B2B methods and servers as are known in the art.

Users may be granted the ability to self-register as Class B users, yet be given full access by the server administrator pending authentication. Specialty Pharmacy users will preferably be able to query physician, patient, and device information from the central administrator for current customers of the server administrator, or of a medical device manufacturer. The Specialty Pharmacy user will preferably supply the central server with periodic electronic reports of prescriptions placed. This report will be redacted to contain no patient identification information, particularly where required by governmental regulation regarding such transactions.

An "Internet Dashboard" GUI may be implemented as the default application start-up display. Preferably, personalization of the GUI is available. Applications must keep track when displayed in a "thumbnail" view or full screen. The default "Dashboard" configuration defines an application suite. The Dashboard will be discussed in more detail below with reference to FIG. 6.

Each application will be able to process user authentication credentials provided by the central server processes, and be capable of operating within the role-based processes defined. Information provided will include a User ID and list of physicians granting proxy rights. This enables applications to request via XML (eXtensible Markup Language) all required information about the user, e.g. visitor's complete name, role (and specialty), and security classification.

Preferably, certain areas will be designated within the server space in which only physicians can grant proxy to other users. The central server will preferably monitor user proxy assignments. The server applications will preferably be able to differentiate between the user logged in and the physician providing proxy authority.

An inactivity timeout may be set on the central server for each login session. A default, e.g., 30 minutes may be set, after which user applications will be closed, and the user will be logged off the server. Separate application level logins are preferably not permitted. After inactivity timeout, return from the pharmacy application will be blocked and re-authentication required. A 4 to 8 digit Pharmacy "Access Code" is permitted upon first entering the pharmacy application.

An application header, or dynamic header section, will be inserted by the central server for display at all times within all applications, independent of Dashboard, GUI, or full screen modes. This ensures persistent connections with active users for security control.

Preferably, disclaimers are linked or displayed near pertinent text, cautioning that site or server use is subject to disclaimer information, or otherwise urging the visitor to read the information, with links to text files containing the disclaimer or policy language. These link interfaces may be entitled, e.g., "Report Interpretation" or "Disclaimer". HTML tables will preferably be used for screen layout, rather than frames, in any server web page.

Preferably, all web pages or server files implementing the present invention will use consistent font faces, font color, and font sizes, with use of tables and images to be negotiated to fit within the display mode parameters.

In a preferred embodiment, data entry forms should fit within an 800×400 application display space without the need to scroll for pages not intended for printing or not detailed reports. Use of "Previous" and "Next" buttons may be used to save current screen contents and go back a step or forward to the next screen respectively. This permits users to set screen resolution to 800×600.

If multiple data records are to be displayed, alternating the use of a light background color is preferred in order to improve readability and reduce errors.

All data entry forms will preferably place the cursor at the first entry field upon load. Design the forms to enable use of the Tab key in moving to the next field, ending with a "Submit" or "Save" button.

Form field entry, and screen display, of Dates will preferably be in the dd-mmm-yyyy format, e.g. 27-DEC-2000. Data conversion code may be made available to automatically switch mm/dd/yy entries to the standard format. A pop-up calendar to select dates is also implemented in a preferred embodiment.

A representative embodiment of the present invention provides utilities and features to improve usability and reduce errors. For example, in fields that require specific data types (numeric vs. alpha), data entry validation is preferably enabled. Upon data entry error, re-entry of the form is enabled to allow correction of the error, preserving data that has already been entered. The cursor may be placed at the field in error for user correction. When selecting critical options (medications/drugs), a pull-down menu is preferably not permitted. Instead, a simple text box with "smart data entry" may be provided to complete the entry when possible. Alternatively, the text may be recorded verbatim.

When a choice of items is exclusive (one or the other) the "radio button" form field type is preferably presented. When a choice of items is inclusive (multiple responses are valid) the "checkbox" form field type may be used. Memo fields, or when text entry may contain more than 80 characters, typically will require the use of the "text-area" form field type.

Detail reports implemented according to the present invention are preferably designed for an 800-pixel width display, but may be scrollable. Format may be displayed in a "Printer-Friendly" layout or provide a separate link to print. Smaller font sizes (down to 8 pt.) are suitable for printable reports. Users may be presented with a "pop-up" notice if it is preferable that they switch their print driver to landscape mode for best results.

Reports that should be printed should include code to automatically pop-up the print dialog box. This will remind the user the form must be printed. The user has only to select which printer to use. If the printed document is to be faxed, preferably a relevant toll-free FAX number, if applicable, is included on the form.

A Login interface may be presented to a user, and may display the server administrator logo, welcome information, username and password fields, plus links for registering for a new account, and forgotten password email form. The URL is preferably mapped to the relevant pages of the administrator entity at the server implementing the present invention. Alternatively the URL may be mapped to a Login.jsp script (optional). The Login interface's purpose is username and password entry, to enable a user to request an account, or displaying a link to an SMTP request or other utility for forgotten user passwords or other failed authentication requests.

Either prior to or following user login, server-to-browser communications preferably switch to SSL (Secure Socket Layer) encryption. The user enters, via keyboard the username and password, executes a Login GUI "button". If user access is approved control is passed to the Preview-Tour (if Class B permission) or Therapy Support Service (TSS) Internet Dashboard (if Class C permission). Preferably, the system is implemented to require that a password must be 7 characters long, including at least 2 numeric characters.

Display response. An invalid username or invalid password may be displayed in red if not confirmed. An inactivity session timeout may be set at a default of 30 minutes, or may be set by the user to an alternate time, e.g., up to 60 minutes.

Upon timing out, the user may be presented with a message that the session timed out, and inviting them to re-login. Following the login process, the user may be presented either with redisplay of Login screen, or may be passed to a "user authorized" page.

With reference to FIG. 3, a "New User" Registration page may be started upon execution of a "New User?" link. This level of registration provides access to the central server for the preview-tour and future personalization of the visitor's dashboard. Only a security class B level of permission is granted.

The New User registration screen collects information about the visitor in a "self registration" process. Asterisk fields may be set as "required" for requesting a basic web account with the server administrator. The script preferably checks for the existence of data in each required field. Required Fields may include User ID, Password, First and Last Name, email, State, Physician (Y/N), and Informational emails (Y/N). Additional required Fields if promoted to TSS access: may include Street Address, City, Zip, and Phone. Optional Fields may include Preferred Name, Salutation, Suffix, address information, and network survey.

A validity check may be provided for, by which if each required field has data, the user is logged out and must log in normally. Usernames must be shorter than 80 characters (common email address length). Data may be stored in TSS database 8 (FIG. 1) tables and held ready for login.

With reference to FIG. 4, a "Forgot Password" or "Contact Server Administrator" link on the LOGIN page is provided. It may consist of a formatted SMTP form to be sent to the destination desired via pull-down menu.

The purpose of the "Contact Server Administrator" email screen is to send private messages to key functional groups or individuals within Server Administrator and/or TSS staff. It is provided (linked) in the Dashboard footer and other footers within TSS applications. The user may input via keyboard the requested information, click on Send, or Clear to re-type the information. Asterisk fields are required for sending a message. The script checks for the existence of data in each required field. Required fields may include First and Last Name, email, State, Phone, and message. Suggested fields may include Email destination (default is forgotten password address). A validity check may be performed to confirm whether each required field has data, the message is sent to the selected destination normally. If not, re-entry of the form for completion is requested. Depending if the field is required, if left blank, a message may be provided to the user to enter the required information for that field, preserving other text as typed.

Figure 13:
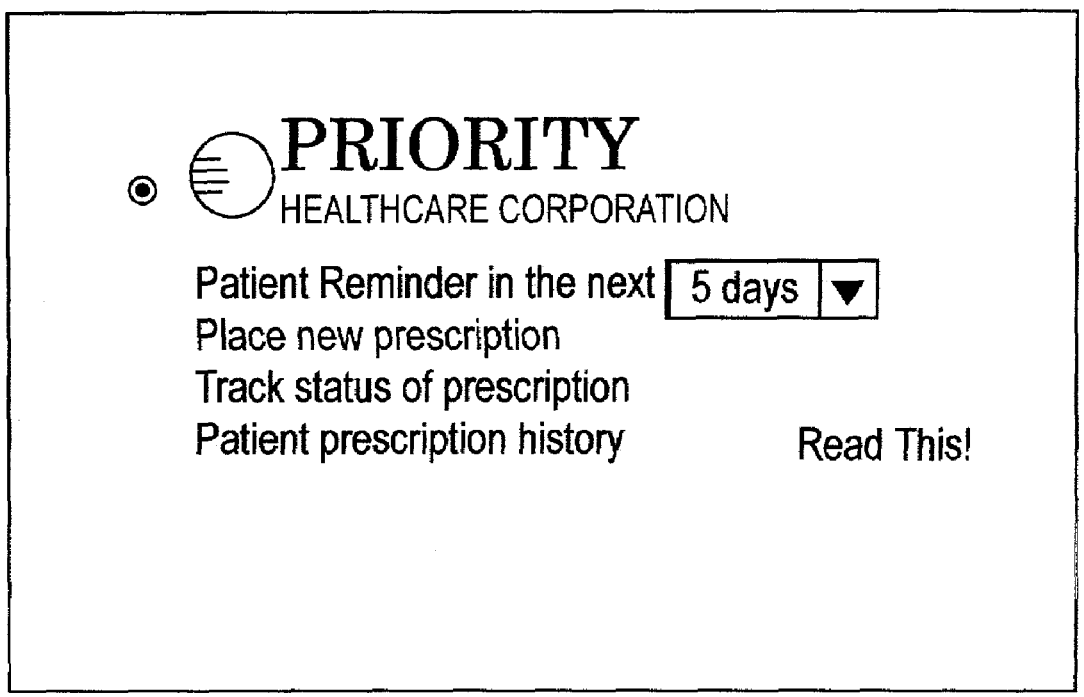
FIG. 13 is a detailed view of the patient management interface of FIG. 4.

According to this embodiment of the present invention, data is incorporated into an SMTP or alternate "e-mail" or messaging format and sent via internal e-mail systems. Email addresses are flexible and may be changed at any time, but are preferably provided for the following scenarios, entities, or individuals: Forgotten Password; Software Use/Help; System Error Report; Device Manufacturer Contact; Drug Delivery Entity Contact; and Internet Development Contact. Refer to FIG. 13 for a more detailed view of the patient management interface of FIG. 4.

Figure 5:
FIG. 5 is an embodiment of a Registration page allowing access to the TSS suite of tools according to the present invention.

With reference to FIG. 5, the present invention preferably provides for authentication and authentication upgrade to TSS application access. The user may be prompted to "Sign-up", via Registration Part 2, to gain access to the TSS Suite of tools. The "sign-up" or registration 2 processes may be implemented to collect user information that the Server Administrator can use to authenticate them as a healthcare professional. If a physician, UPIN (Unique Physician Identification Number) and DEA (Drug Enforcement Agency) numbers are collected. All users may be required to enter a State License number. The information may be submitted by execution of the Submit GUI button, or Clear may be executed to re-type the information.

Asterisk fields are required for authenticating the user. The script checks for the existence of data in each required field. Preferably, required fields include SSN (Social Security Number), UPIN, DEA, State License No., Profession, and Home/Office/Hospital phone, as well as expiration dates on DEA and State License No. Profession may be implemented as a pull-down selection to enable a sortable field. If the field is required, but left blank, a message may be provided to the user to enter the required information for that field, preserving other text as typed. An algorithm for DEA number validation is computed upon data entry and tab or clicking to the next field. The DEA number always starts out with an A or B followed by another letter. The first letter is A for physicians who received their numbers before approximately 1980; thereafter they begin with B. While this may not be a hard and fast rule, it is generally true. The next letter is simply the first letter of the doctor's last name. Next comes a seven-digit registration number. The final digit of this number is called the "check digit". The "check digit" is used to verify the rest of the number by processing it with the proper algorithm. The algorithm is as follows: the "check digit" will equal the last digit of the sum of a) the addition of the 2nd, 4th, and 6th digits times two PLUS b) the sum of the addition of the 1st, 3rd, and 5th digits. Expiration dates may not be needed on some authenticators. Validation testing will confirm actual practice (sometimes by state) and adjust the data entry validation scripts as needed. Document any changes in the Validation Test Checklist report(s). The User Data is saved in TSS database 8 for Administrative review and action.

Physical communications, e.g. over POTS, between the Server Administrator staff and the customer may be provided to confirm account creation, assign a password, and set security Class C for TSS access. A maintenance screen is provided for the TSS consultant to review the user's credentials, call to confirm, change the password, and switch the account to active.

Figure 6:
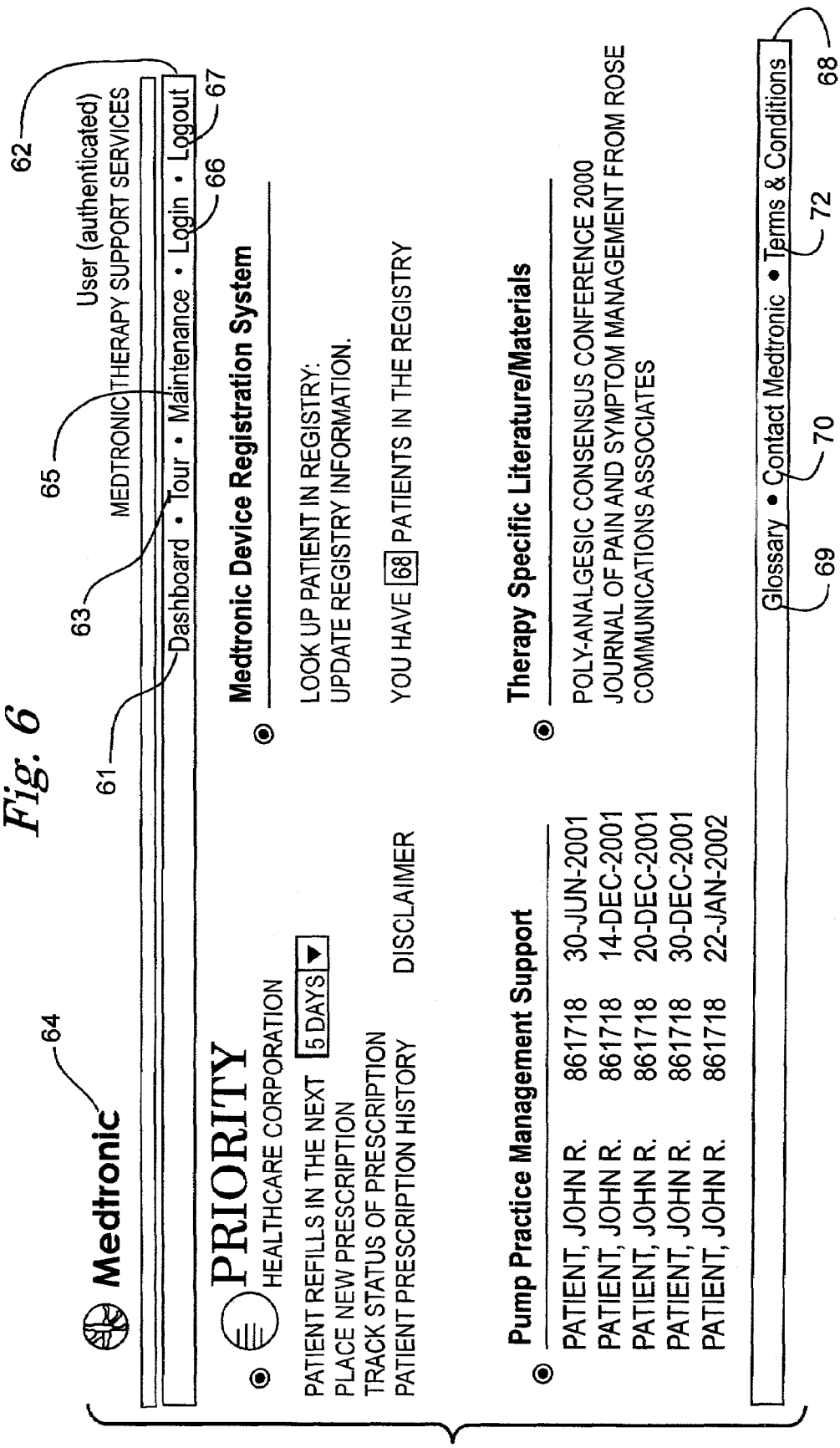
FIG. 6 is an embodiment of the Internet Dashboard implemented as a static web page according to the present invention.

With reference to FIG. 6, the "Internet DASHBOARD" or "Server application portal" is a standard Portal to Server Administrator applications. The Dashboard may be implemented as a static web page, and may provide a "home page" for TSS applications. The purpose of the Dashboard is to launch all TSS applications and display "thumbnail" or small window views of each. User commands and messages can be displayed in the small window views. Each application is preferably being executed, or running "live", rather than being simulated, even in thumbnail view. A standard TSS header may be included at the top to enable positive identification of who is currently active, and to provide consistent navigation between the Dashboard, Tour, and User Maintenance functions, plus the Login/Logout functions through their respective links on menu bar 62.

Executing "Server Administrator Logo" 64 may open a pop-up browser window to a Server Administrator web page or server file. Executing "Dashboard" link 61 will switch to the Dashboard from TSS applications, or if the Dashboard is currently displayed, will refresh the display contents. Executing "Tour" link 63 will switch to a full screen Preview-Tour that will provide a navigation bar link back to the Dashboard. Executing "Maintenance" link 65 will preferably switch to the user's basic account information for update and changes. Preferably the password may be changed at any time. Executing "login" link 66 will log the current user off the system and display the Login page for another user to login. Preferably, for security reasons, a login screen inactivity timeout of 1 minute is set; upon expiration the screen will switch to a central server web page or server file. Executing "Logout" link 67 or GUI button will log the current user off the system, and may display the home page of the server administrator or some other entity.

A static Table data structure is used within the body of the Dashboard, one for each core application described above. Java/JSP server side includes, and command parameters manage the startup/launch of each application. Microsoft ASP, Java/JSP, and HTML/JavaScript applications will preferably be supported.

User authentication is passed to each application via an XML credentials exchange. Preferably with each application, a standard TSS Footer is included at the bottom to identify the version number, copyrights, and links to key commands (shown below).

Footer Commands and Links are provided on the Dashboard on menu bar 68. Executing "Glossary" link 69 opens a pop-up browser window to a Server Administrator standard terms index. Terms and their definitions may be indexed in alphabetical order. Executing "Contact Server Administrator" link 70 will switch to the TSS email form. This may be the same form as the Forgotten Password link. However, users may direct their email to any destination in the pull-down list. Executing "Terms & Conditions" link 72 will switch to a pop-up browser window of the Server Administrator Web Site Terms and Conditions page. This may be a summary of legal and privacy information that the user needs to have access to when using the site. A Print command is preferably provided in the page.

Particular applications may be provided for Specialty Pharmacy entity Applications, Device Registration Systems, and Physicians' Pump Practice Management (PPM) Support.

Figure 14:
FIG. 14 is an embodiment of the pump practice management interface according to the present invention.

With reference to FIGS. 7 & 14, the PPM application may provide Pump Replacement Report 74. It provides a standard battery functional longevity estimate based on the pump Technical Manual. The purpose of the device longevity report is to provide an early warning to physicians when to expect battery depletion or other device limitations or conditions, which may indicate device replacement. This enables them to appropriately plan for a replacement device and the replacement procedure. Preferably, the device longevity report will utilize current information in the industry, and specific empirical data pertaining to a certain device, or production run of a device, which may present variations in specified longevity.

Input data is provided via the Server Administrator Device Registration System for patient records the user has permission to view. Based on the pump model number, the mean longevity may be estimated in months with +/−3 standard deviations. Months may be converted to actual dates based on implant date. "Calculate" button 76 links the specific patient data to the calculate function of the report. For example, a certain model of pump may have a statistical mean longevity of a certain number of months and Standard Deviation (SD) of some other month value. In any event, the Report will preferably be formatted for printing via the browser print icon. Records with −3SD within the current date are displayed in bold red for visibility and to alert the user to a device implantation which may warrant attention. With reference to FIG. 8, displayed fields of the application may include Patient Name, Pump Model, Implant Date, −3SD, Mean, and +3SD. "Calculate" button 76 from the main report may cause to be displayed a longevity calculator that compensates for average daily infusion volume. This typically provides a much more accurate battery functional longevity estimate and is based on the pump technical manual. The purpose of the device longevity calculator is to provide a better estimate of expected battery depletion. The 3-year spread of the PPM report can be reduced to a number of months. It is dependent upon the accuracy of the physician's estimate of average daily infusion volume.

Input data may be provided via the physician in the form of an Average Daily Infusion Volume or "Daily Rate". Based on the pump model number, formulas determined by regression analysis of pump performance data may be used for the mean longevity by daily rate and standard deviation by daily rate.

Statistical Formulas may be determined for various types of pumps. For example, a certain pump model may have the following values:

R−Sq=100%, R−Sq(adj)=100%
MONTHS=50.9405−15.3033*RATE+ 3.97768*FLOW^2−0.562651*FLOW^3
SD=2.69002−1.54168*RATE+0.464456*FLOW^2− 0.0153476*FLOW^3

Or another may have values as follows:
R−Sq=99.8%, R−Sq(adj)=99.7%
MONTHS=104.710−63.6444*RATE+ 27.4476*FLOW^2−5.17339*FLOW^3
SD=8.15098−6.45716*RATE+6.75589*FLOW^2− 2.51996*FLOW^3

The calculator may display a printer icon to print the result.

Displayed fields for this function will preferably include Patient Name, Pump Model, Implant Date, −3SD, MEAN, +3SD. It may be advisable to display a disclaimer on the calculator.

With reference again to FIG. 7, therapy-Specific Literature and Materials may be provided in an application: The Literature & Materials may be implemented as a simple HTML-JavaScript application for sharing on-line information. The purpose of the Therapy Specific Literature & Materials tool is to provide on-line information, downloadable user guides, and a business reply card (BRC) for ordering reprints, for example, from the Server Administrator, Device Manufacturer, or a business partner. This application may also include an on-line catalog of Server Administrator clinical and technical publications as well as independent third-party publications.

Links to desired information may be executed for download, to start a BRC order form, or to enable HTML display of Server Administrator/TSS contact information. Downloadable Files will preferably be provided in HTML, plain text, or in Adobe PDF file format with trailing PDF icon. Referenced Contact & Support page will preferably have a TSS header and BACK or CLOSE link. A Disclaimer link may be provided with popup display of legal information with "PRINT" and "BACK" or "CLOSE" links. The Therapy Specific Literature Application may be provided with a Business Replay Card function. This may be a reprint order form sent directly to the Server Administrator The BRC tool may be implemented in order to provide for on-line requests for information that Server Administrator cannot directly provide nor promote. This publication is available for healthcare professionals upon their request. A third party, for example, may send the requested information directly to the requester. The application may require that the request include requesters name, address, profession, practice/department (if available), and phone/fax numbers. A disclaimer link may be provided with pop-up display of legal information with PRINT and BACK or CLOSE links.

The TSS site, including the Dashboard and component JSP applications, should be accessed via a standard SSL capable web server in communication with an SSL capable application server in communication with third party servers. All application code may be processed via off the shelf software running on standard configuration hardware platforms installed per vendor instructions. There is preferably no direct interface between TSS applications and server hardware.

The Therapy Support Services (TSS) system may be implemented so as to interact with other systems through WebMethods Enterprise. Specialty Pharmacy application 6 may be implemented to interact with Microsoft ASP application server and WebMethods Partner server both running on remote Windows 2000 systems. All database communications with trading partners may be accomplished with WebMethods B2B and Partner servers. Java Servlets may be used for all or portions of individual applications. XML will be implemented for B2B document exchanges, such as when passing user credentials and sending periodic system reports.

Data communications over the Internet space should be encrypted via SSL IP-Secure or a Virtual Private Network (VPN). This includes client to server and server to server. No direct communications connections will preferably be enacted between business partners and Server Administrator clients (users) without provision for monitoring and ensuring persistent connections and other security concerns.

Where patient private information is shared between healthcare clients and Specialty Pharmacy 6, the Server Administrator should not store, monitor, or access this information without signed patient consent, to the extent that any government or industry standards so require. TSS database 8 may be implemented in any number of third party database engines, e.g., Oracle. TSS database 8 will contain detailed information about associates (physicians, nurses, etc.), Server Administrator device patients, devices, redacted or "scrubbed" prescription records, and user profiles. Access to database 8 may be through the TSS System or adapters created for WebMethods Enterprise.

Access to applications and patient information by a non-physician may take place via proxy rights granted by a physician within the same medical practice. Proxy relationships may be monitored and maintained by TSS system administrators. Periodic verifications will be conducted of proxy settings. Access to the "Device Registry" may be limited to Read-Only with filtering enabled to display only certain products/patients. Only fields required by the application are displayed within the applications. Only those patient records the client supports are viewable by the client.

TSS database(s) 8 and web site will preferably be backed up nightly to magnetic tape, with standard Server Administrator Information Technology (SAIT) tape rotation algorithms established. Archive tapes are to be stored off site for disaster recovery.

This system will preferably utilize SSL to encrypt communications with the user's browser and the server administrator's business partner's web server(s). All communications over the public Internet are SSL, including XML document B2B exchanges between servers. This will typically be sufficient for Class B & C users. Class D users will also preferably utilize SSL and will initially be required to connect from the Server Administrator Intranet. This ensures that the class D user is physically at a Server Administrator facility or is logged in using Nomad and SecureID card.

Advantages provided via the Present Invention are a single Login and scaleable authentication process, and provision of a customer-centric site organization through personalized dashboard (user preferences). The invention also provides shareable applications between businesses, and enables a server administrator to engage in customer relationship management. The invention may be made customizable by Therapy, Market Segment, etc., and may be organized along multipurpose lines, e.g., Marketing, Patient/Tech Support, etc.

The invention may be implemented to supports all types of customers & employees of a medical device manufacturer or server administrator, as well as physicians, nurses, hospital professionals, administrators, and patients, family, friends/support. The invention may be implemented with integral Command center/help desk support, and will provide FAQ publications, consistent user manuals, a WebEx tool for consultation, and remote control of devices. The application will provide minimal standard navigation overhead and will preferably be implemented in a way that minimizes development costs through a standard header and footer, CMS templates for developers, sample code, utilities, shared screens. Also in this regard, a B2B-WebMethods middleware Infrastructure will provide a standardized framework for development.

Figure 15:
FIG. 15 is an embodiment of the business partner interface according to the present invention.

Again with reference to FIG. 6, a "Suite", which may be defined as any collection of central server applications, may include a custom title for each suite, e.g. "Therapy Support Services". The four TSS core applications according to a present embodiment of the invention are assigned to the suite definition (two are "shareable"). In the present implementation of the invention, the TSS dashboard layout is set to a "4×4" format with each application assigned to one of four corner locations within the central interface. The user will preferably be permitted to mix and match any shareable application available on central server, via "thumbnail" or windowed views. The present application provides support for diverse application concepts, and applications may be implemented at the browser side in a "plug-and-play" style implementation as shown in FIG. 14. This example application is wrapped in the standard central server header, yet uses left-side navigation for the three primary commands. The footer format remains consistent, yet reflects the application's version number. The example application of FIG. 15 is wrapped in the standard central server header, yet uses top navigation/commands for the multiple commands. The footer (not shown) preferably remains consistent, yet is provided by the B2B partner, and reflects their application version number, contacts, etc. In this implementation the partner's application is running Microsoft® application scripts. Each application preferably records its "address" within the CMS dashboard suite. An option may be provided to permit user-personalized thumbnail arrangements, or a custom suite. The access audience for each application may be defined by role or specialty, with associated applications defined by title and permissions, with corresponding dashboard configuration and application location assignments, accessible via a unique URL. Entry of a URL provides a direct link to the TSS suite (via user login). Each Application will preferably be registered with a Suite, and will supply an application title, owner, contact, and version, defining an access audience defined by role/specialty.

Applications may be shareable or not, as between different categories of medical professionals or persons interested in different implanted devices. For example, Specialty Pharmacy and Pump Practice Mgmt Support may be unique to a TSS for implantable therapeutic substance infusion devices. In contrast, Device Registration System and Therapy Specific Literature/Materials applications may be shared with any central server suite implemented by a device manufacturer, ISP, ASP, or other server administrator. Applications will preferably always include the navigation header and footer, and will preferably support dual screen modes (Thumbnail or windowed display mode as compared to Full-screen display mode). Preferably, the applications interfaces fit within an 800×600 screen (minus the central server header space), in order to provide interactive applications without scrolling. It may prove preferably in a specific implementation for all commands, buttons, links, and disclaimers and legal notices to be clearly identified via linguistic or visual cues, e.g. "Read This!" Complete terms and conditions of server use and access should preferably be available within or linked by footer bar. The applications should provide security and access permissions according to user role and specialty-based access, and support LDAP directory access control. Sessions should be effected according to SSL encrypted communications.

Applications will preferably be coded using open standards JSP scripting, and will support common html browsers, e.g., Netscape and Internet Explorer 4+, minimize use of compiled JAVA Applets, use JavaScript or another scripting language that supports all or most popular Internet browsers, and provides for data access calls via WebMethods or an alternate suitable middleware utility.

FIG. 9 is a diagrammatic representation of a connectivity system according to the present invention. The diagrammatic representation of connectivity system 9 shows the interaction between the pharmacist 14, clinician 12, drug pump manufacturer 18, and patient 10. Patient 10, clinician 12, prescription provider 14, drug database 16, and drug pump manufacturer 18 all have connectivity to one another over a data communications network, which may include a public internetwork such as the Internet. In the present invention, patient 10 may be provided the capability to exercise some control over their own therapy as warranted or as permitted by clinician 12, as well as providing via an implanted drug pump or other implanted medical device, detailed physiological data pertaining to patient 10 such as heart monitoring, respiration monitoring, or temperature monitoring. Drug pump information and the patient's physiological data are communicated to a central location 20, which for the purposes of the preferred embodiment may be the device manufacturer or central server administered by the device manufacturer, depicted as server 20. Once the central server 20 has the drug pump and patient physiological data, the data is then inputted into a database 22, depicted as a drug pump manufacturer database "MDD.com Data Base" 22.

When clinician 12 registers the implantable drug pump's serial number via connectivity system 9, he or she may be provided with extensive information regarding the implanted pump. Clinician 12 is able to discover such information as whether a specific catheter is compatible with certain therapeutic substances, therapies or stress forces that the pump places on the therapeutic substance during pumping at different pumping rates. For example, certain stresses on therapeutic substances, such as pressure, alter the therapeutic substance through the actual pumping activity, such as a biologic or genetic material, which have constraints on the types of stresses the material may be exposed to before affecting the therapeutic properties of the agent. Therefore, having all of the implantable drug pump information assists clinician 12 in developing the intrathecal or other substance-release therapy and selecting an appropriate therapeutic agent.

Since clinician 12 can obtain extensive information in regard to the implantable drug pump, care of patient 10 may be improved. By optimizing the capabilities of the implantable drug pump and the capabilities of the therapeutic substances, patient 10 may be expected to benefit. For example, by optimizing the capabilities of the implantable drug pump and the capabilities of the therapeutic substances, as well as more accurately predicting the expected life of the drug pump, without providing for an overly conservative regimen or projected life for the device, or the treatment life of the drug pump, the life of the implantable drug pump can more accurately be determined and therefore the patient would not need their pump explanted until a later time. This benefits patient 10 and the insurance company that may be paying for the explanting procedure.

Another advantage to connectivity system 9 is that drug pump manufacturer 18 can receive instantaneous positive and negative feedback from all of the stakeholders. For example, by examining the extensive information feedback from clinicians drug pump manufacturer 18 can discover that the pump is operating longer than they had expected it to and thus allow for the extension of the pump's expected life. Another example is where drug pump manufacturer 18 examines the extensive feedback information and discovers that in particular pumps a certain gear is failing at a time earlier than expected. Since drug pump manufacturer 18 knows this information they can instantaneously target the specific clinicians and patients that really ought to be concerned about that particular pump.

With reference again to FIG. 9, a clinician 12 is able to directly communicate a prescription change to pharmacist 14 via connectivity system 9. Clinician 12 inputs the prescription change and when the database receives the prescription change pharmacist 14 is immediately notified of the prescription change.

Figure 10A:
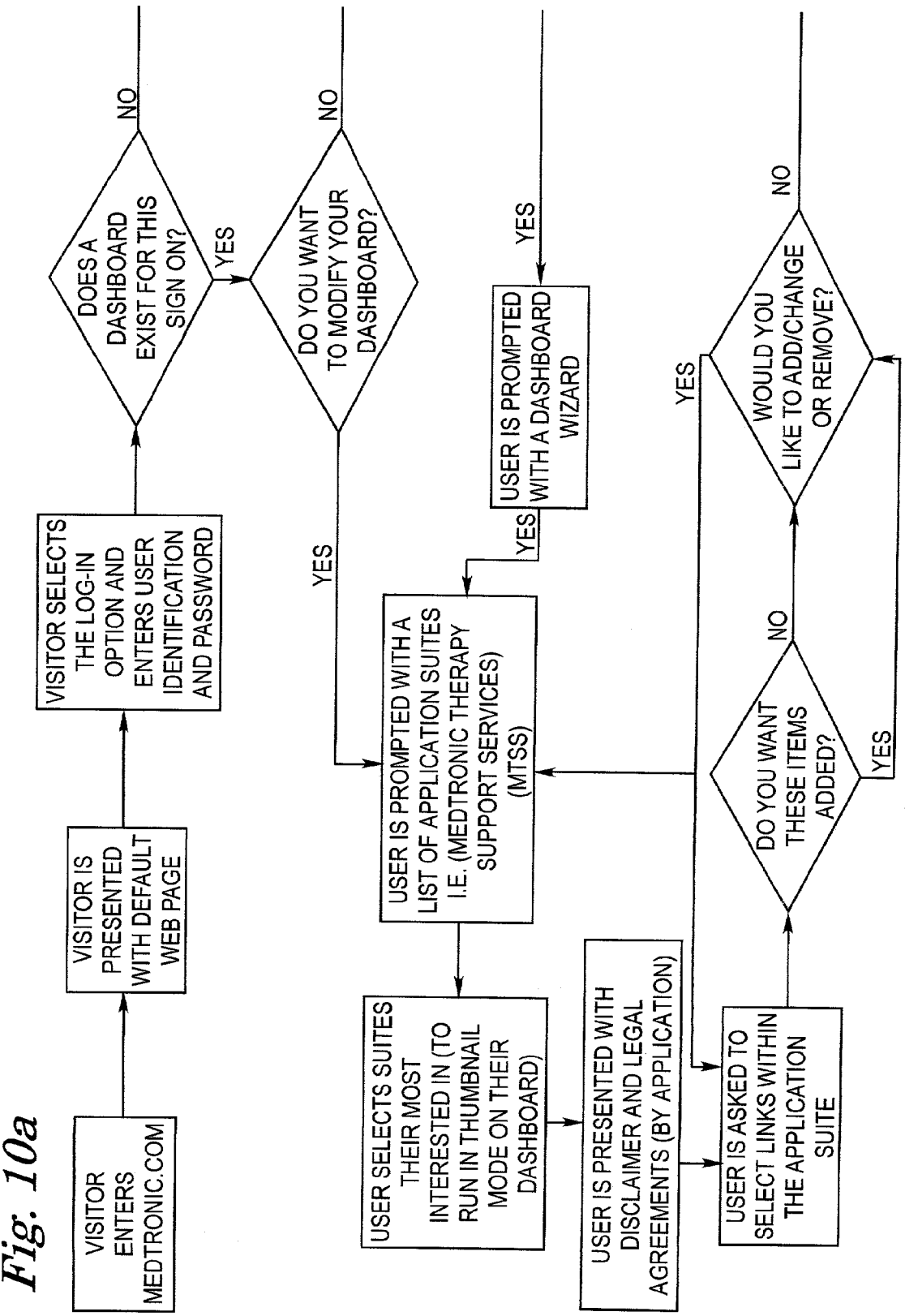
FIG. 10 is a data flow/state transition diagram for the navigation of a user through a clinician server of the present invention.
Figure 10B:
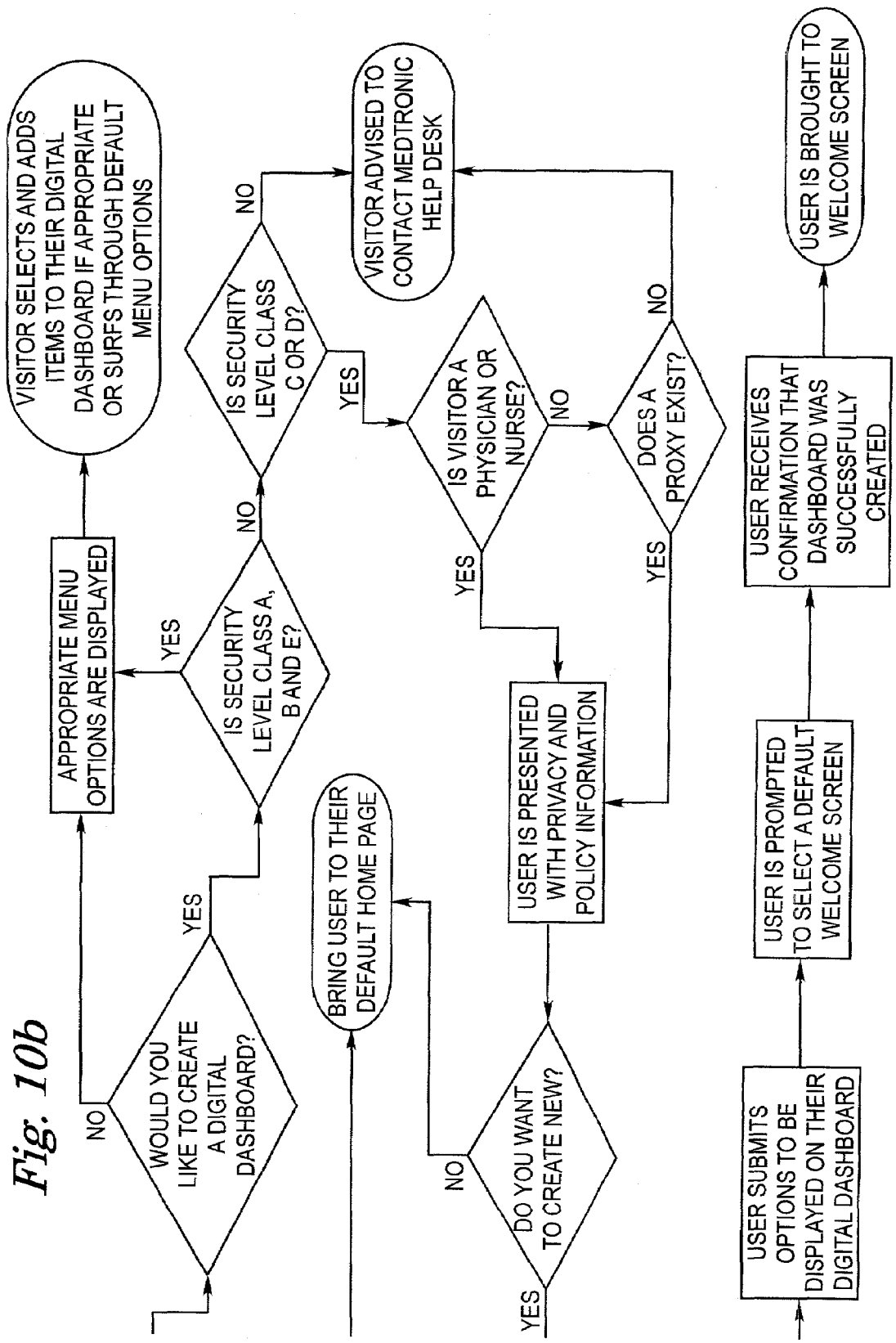

FIG. 10 depicts a data flow/state transition diagram for the navigation of a user through a clinician server of the present invention, providing for the creation and/or modification of a user interface according to the invention. In a preferred embodiment, when the user enters the "home page" for the TSS applications implemented as a static web page, they are presented with a default web page. Here, if the user decides to login, they will enter their user name and password. The application then determines if a personalized "dashboard"

already exists for the user. If not, then the user is asked if they would like to create a personalized "dashboard".

If the user decides not to create a personalized dashboard, then the user is allowed to navigate through the application with default menu options. If the user decides to create a personalized dashboard, then the application navigates the user through the security level registration process discussed in detail above and shown in FIG. 10. After the security registration, the user is presented with the applications privacy and policy information to inform the user of their rights while using the application. The user is then asked if they would like to create a new personalized "dashboard". If the user decides not to, then the user is routed to their default or existing personalized "dashboard".

If the user does decide to create a new personalized "dashboard" or even to modify an existing "dashboard", then they are presented with a "dashboard wizard", which assists the user in developing their personalized TSS WebPage. The user is prompted with a list of application suites, such as those described above and below with reference to FIG. 12. The user then selects the suites they are most interested in and within these suites the user is asked which items they would like to add, change, or remove. When finished, the user submits the options to be displayed on their digital dashboard. The user is then prompted to select a default welcome screen. The user is then prompted to confirm that the dashboard was successfully created. Upon confirmation, the user is then routed to their welcome screen and they can begin using the applications they have chosen for their personal dashboard.

Figure 11:
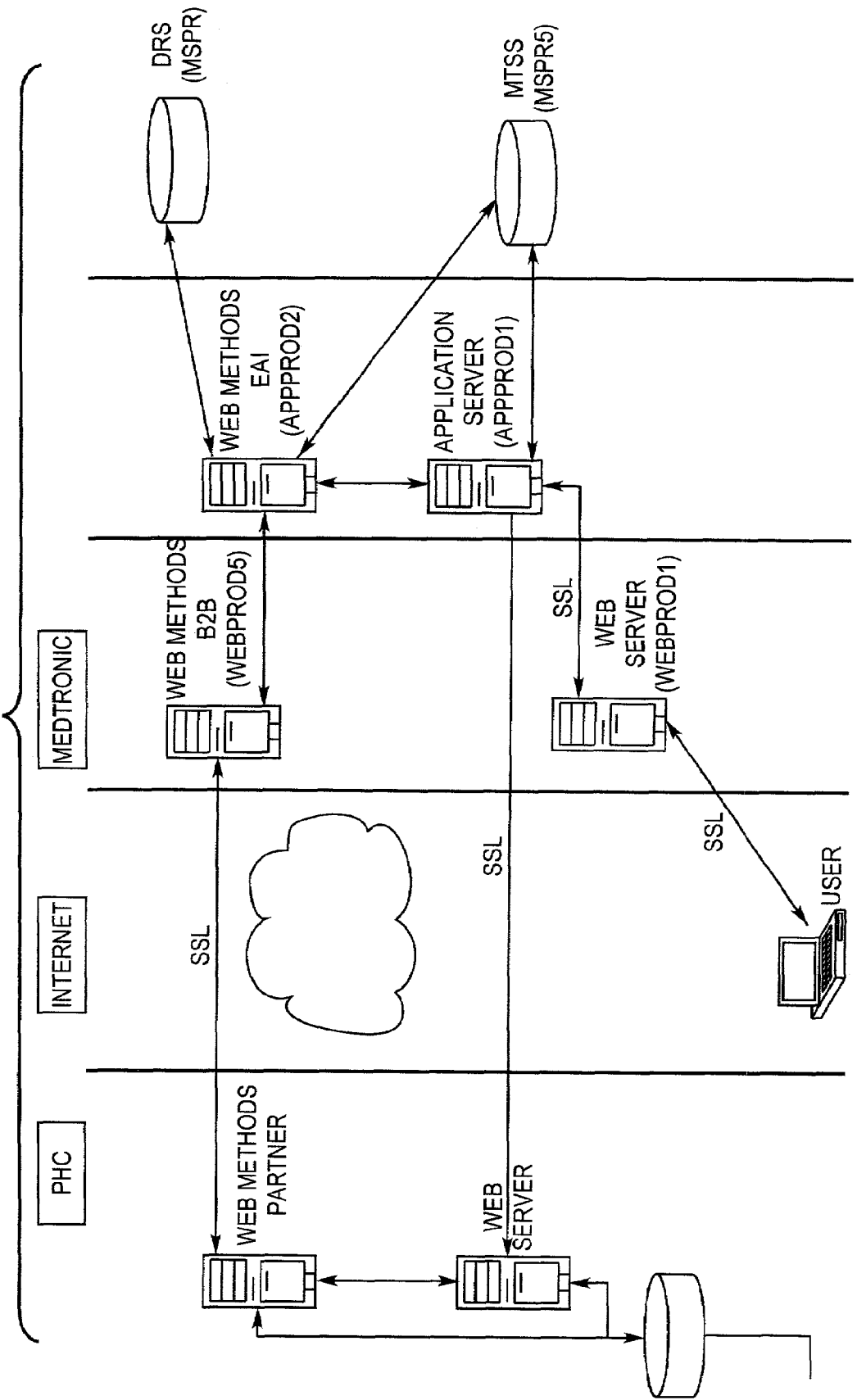
FIG. 11 is an entity demarcated network diagram of a representative business partner and server administrator communication arrangement according to an embodiment of the present invention.

FIG. 11 depicts an entity demarcated network diagram of a representative business partner and server administrator communication arrangement according to a representative embodiment of the present invention. The business partner to the server administrator may be, for example, a therapeutic agent dispensary or pharmacy.

Figure 12:
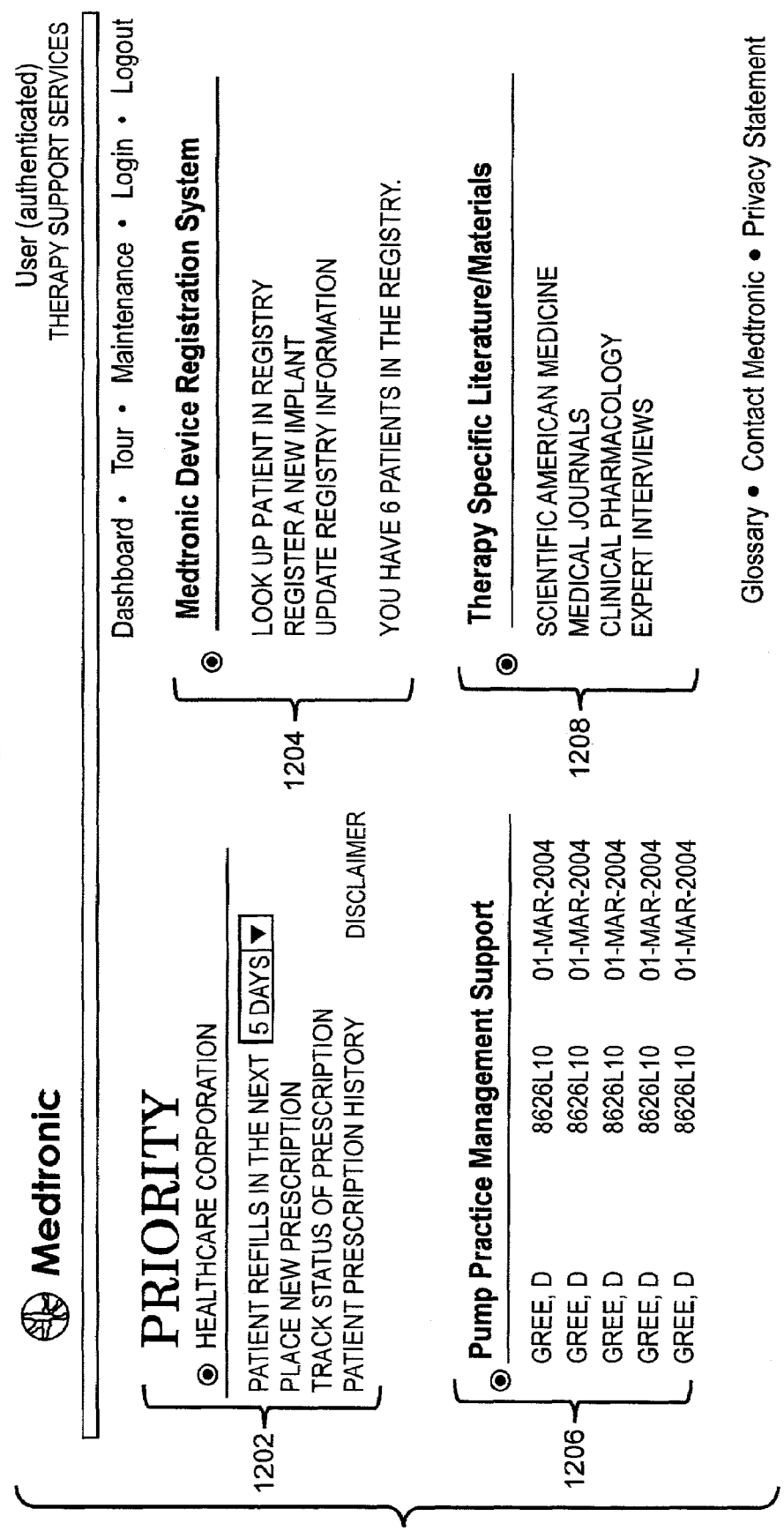
FIG. 12 is one embodiment of a user interface for the TSS server, according to the present invention.

FIG. 12 depicts a possible implementation of a user interface of the TSS server, according to the present invention, depicting the primary user applications available. The user is provided with a front-end interface, which may be implemented as a static configuration of four interactive web applications running in a "thumbnail" or windowed mode.

The initial suite will include an Internet GUI Application Portal that will preferably display the primary available applications provided to users by the system. Preferably, the GUI will be a user-configurable template. The Applications may be integrated into the GUI using Server-side or JSP "includes". Users may be provided with the ability to maintain their own addresses and non-secured user account information.

The first application (box 1202) in this suite may be termed a "Specialty Pharmacy" application. The application provides an on-line automated dose calculator, which provides for "What-if" scenario planning of various contemplated or alternate treatment regimens. It allows a physician to order therapeutic agents and their respective refills as needed through connectivity system 9. The application also allows the physician to change a therapeutic agent as necessary. The application will provide reminders when a prescription is due to be refilled. As stated above, typically a 4 to 8 digit Pharmacy "Access Code" is required upon a clinician first entering the pharmacy application.

The second application box (1204) of the suite, according to the present invention, may be termed a "Device Registration System" ("DRS") lookup and update. This application provides for the management of implanted therapeutic substance infusion devices. It allows the user to register an implantable therapeutic substance infusion device with the devices manufacturer as well as provide feedback to the manufacturer regarding the operation of the implanted therapeutic substance device of the lifetime of the device. A user can access reports that detail a therapeutic substance infusion device's capabilities and interconnectivities with other devices.

The third application (box 1206) is labeled a "Pump Practice Management Support and Replacement Report" application. This will preferably provide for a "Pump Replacement Report" to estimate battery End-Of-Life for implanted pumps. The report is based on an algorithm provided by the device manufacturer. The report preferably provides minimum, maximum, and predicted failure dates. This feature allows the physician to contact the patient, e.g., through a communication network and schedule a replacement before the pump alarm is triggered.

The fourth application (box 1208) labeled "Therapy Specific Literature and Materials" operates as a server file or "web page" providing links to other files containing technical news, articles, and educational materials. Therefore the user can inform themselves about the devices they are working with as well as keeping up to date on the latest developments with devices, which are already implanted.

Figure 16:
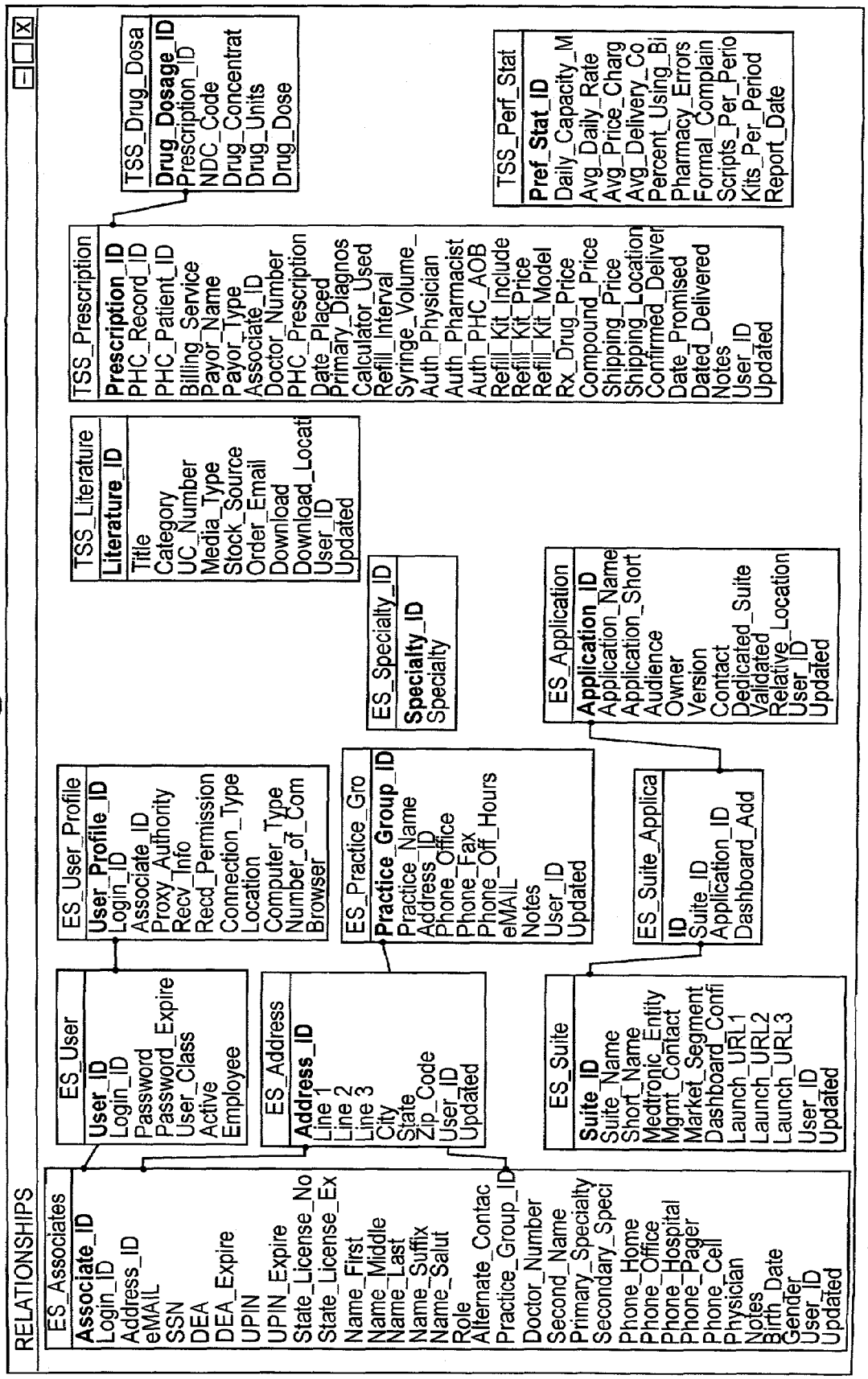
FIG. 16 is a representation of a class-based development implementation of a server application according to the present invention.

FIG. 15 shows a suitable implementation of the business partner interface according to the present invention. A suitable class-based development implementation of a server application according to the present invention, showing suitable classes, class relationships, and member data types, is shown in FIG. 16. In a preferred embodiment, a system implementing the present invention provides access to a Full-service Specialty Pharmacy, with patient-specific dispensing of therapeutic agents. The invention also provides for automated reimbursement/billing support and assignment of benefits between payors, care providers and clinicians, patients, pharmacies and dispensaries, and producers, manufacturers, and supplies of health care supplies, equipment, and materials.

In order to provide added convenience in the administration and servicing of drug pumps, the invention provides for a prescription-ordering database, and provides users with pump refill or prescription order reminders, that may be presented to a user via a data network. Also according to the present invention, a national pharmacy with ASHP quality standards may be operated, with comprehensive continuous, 24-hour pharmacy support. Clinicians may be provided with on-line patient prescription history and charts, on-line device registration, a medical device replacement report or scheduler to provide reminders of upcoming device replacement priorities, a utility providing for SMTP or other electronic messaging between clinicians, device manufacturers, and key management and service partners, and integration with pain management ventures and recommendations to physicians. In a preferred embodiment, the present invention is implemented as an on-line replacement for paper forms and reports. Accordingly, electronic signatures are provided for so as to comply with requirements for secure and authenticated electronic medical records. Alternatively, the present invention may be configured to generate paper forms and reports as the official record if desired by a clinician or otherwise required.

Certain government regulations in several nations provide for requirements of data security and patient information privacy, particularly when an individual may be identified from the data being considered. Accordingly, automated reports between entities are preferably having patient identifying information redacted; yet preserve the prescription history objective for each individual record. Alternatively, digital encryption and authentication via digital signature technology may be provided for.

It will be appreciated that the present invention can take many forms and embodiments. The true essence and spirit of this invention are defined in the appended claims, and it is not intended that the embodiment of the invention presented herein should limit the scope thereof.

What is claimed is:

1. A computerized system providing for the management and configuration of one or more therapeutic substance infusion devices, comprising:
    a server connected to a network, said server further being connected to a database of patient information;
    a remote suite of computer readable remote program code devices for support of therapeutic substance infusion devices connected through said network comprising:
        a first computer readable remote program code device adapted to permit a user to provide feedback to a therapeutic substance infusion device manufacturer regarding the operation of the one or more therapeutic substance infusion devices;
        a second computer readable remote program code device which allows the user access to a report including information on therapeutic substance infusion device patient support and device replacement management;
        a third computer readable remote program code device which allows a user access to literature providing information concerning therapeutic substance infusion devices;
        and a fourth computer readable remote program code device which provides a communication connection between a clinician and a pharmacy.

2. The computerized system of claim 1, wherein the first computer readable remote program code device allows the user to register a therapeutic substance infusion device with the medical device manufacturer.

3. The computerized system of claim 1, wherein the first computer readable remote program code device allows the user to view a therapeutic substance infusion device's capabilities and interconnectivities.

4. The computerized system of claim 1, wherein the second computer readable remote program code device allows the user to view a list of therapeutic substance infusion devices implanted in one or more patients and schedule events pertaining to these devices.

5. The computerized system of claim 4, wherein the second computer readable remote program code device allows the user to view at least one patient's prescription history and medical history.

6. The computerized system of claim 4, wherein the second computer readable remote program code device predicts a lifespan of at least one therapeutic substance infusion device.

7. The computerized system of claim 6, wherein the predicted lifespan is based on an algorithm provided by the therapeutic substance infusion device manufacturer.

8. The computerized system of claim 7, wherein the algorithm performs calculations for therapeutic substance infusion device replacement based on information learned by the therapeutic substance infusion device manufacturer on therapeutic substance infusion devices in an existing patient population.

9. The computerized system of claim 8, wherein the predicted lifespan includes a minimum life expectancy, a maximum life expectancy, and a predicted failure date for the at least one therapeutic substance infusion device.

10. The computerized system of claim 4, wherein the second computer readable remote program code device provides the user with a therapeutic substance infusion device replacement schedule to provide reminders of upcoming device replacement priorities.

11. The computerized system of claim 1, wherein a server file or a web page is accessed to provide access to the literature concerning therapeutic substance infusion devices.

12. The computerized system of claim 11, wherein the literature is specifically targeted to the user's areas of interest.

13. The computerized system of claim 1, wherein the fourth computer readable remote program code device allows the clinician to place orders of a therapeutic agent on behalf of a patient.

14. The computerized system of claim 13, wherein the fourth computer readable remote program code device allows the user to change prescription orders of a therapeutic agent on behalf of a patient.

15. The computerized system of claim 1, wherein the fourth computer readable remote program code device provides the user with an automated dosage calculator to provide predictive scenarios of contemplated treatment regimens.

16. The computerized system of claim 1, wherein the fourth computer readable remote program code device provides the user with at least one of pump refill reminders and prescription order reminders.

17. The computerized system of claim 1, wherein at least one computer readable remote program code device is implemented as an Internet graphical user interface application portal.

18. The computerized system of claim 17, wherein the graphical user interface is a user-configurable template.

19. The computerized system of claim 17, wherein the Internet graphical user interface is implemented with at least one of Java and HTML technologies.

20. The computerized system of claim 1, wherein the server hosts a first computer readable server program code device for the entry of patient information into the database of patient information.

21. The computerized system of claim 20, wherein the server is further connected to a database of therapeutic substance infusion device information.

22. The computerized system of claim 21, wherein the server further hosts a second computer readable server program code device for the entry of therapeutic substance infusion device information into the database of therapeutic substance infusion device information.

23. The computerized system of claim 22, wherein the sewer is further connected to a database of user profiles.

24. The computerized system of claim 23, wherein the server further hosts a third computer readable server program code device for the entry of user profile information into the database of user profiles.

25. The computerized system of claim 24, wherein the server is further connected to a database of therapeutic agent information.

26. The computerized system of claim 25, wherein the server further hosts a fourth computer readable server program code device for the entry of therapeutic agent data into the database of therapeutic agent information.

27. The computerized system of claim 26, wherein the server hosts a fifth computer readable server program code device for the accessing and analysis of therapeutic agent data as applied to at least one specific patient.

28. The computerized system of claim 27, wherein the fifth computer readable server program code device determines compatibility with at least one therapeutic substance infusion device.

29. The computerized system of claim 28, wherein the therapeutic agent data comprises recommended dosages and agent interaction data.

30. The computerized system of claim 20, wherein the patient data further comprises therapeutic agent allergies for at least one specific patient.

31. The computerized system of claim 30, wherein the fifth computer readable server program code device provides therapeutic agent refill and order reminders.

32. The computerized system of claim 31, wherein access to the server is provided to third party users over a secure virtual connection over a public network.

33. The computerized system of claim 32, wherein the third party users include at least one of a pharmacist, a physician, a patient, and the therapeutic substance infusion device manufacturer.

34. The computerized system of claim 33, wherein the access to the server is provided following encrypted knowledge-based authentication.

35. The computerized system of claim 34, wherein the access to the server is provided following receipt of a passphrase over an encrypted channel.

36. The computerized system of claim 35, wherein access to the server is provided over a secure socket layer protocol connection.

37. The computerized system of claim 36, wherein the connection of the server to the network is a business-to-business connection with at least one therapeutic agent dispensary.

38. The computerized system of claim 37, wherein the connection of the server to the network is a business-to-customer connection with at least one physician.

39. The computerized system of claim 38, wherein the connection of the server to the network is a business-to-customer connection with at least one patient.

40. A computerized system providing for the management and configuration of one or more therapeutic substance infusion devices, comprising:
a server connected to a network;
a database of patient information connected to said network;
a database of therapeutic substance infusion device information connected to said network;
a database of therapeutic agent information connected to said network;
a database of user profile information connected to said network;
a suite of computer readable remote program code devices for support of therapeutic substance infusion devices connected through said network including:
a first computer readable remote program code device that allows a user to manage therapeutic substance infusion devices, said first application allowing the user to register a therapeutic substance infusion device with a medical device manufacturer;
a second computer readable remote program code device that allows the user access to a report which includes information on therapeutic substance infusion device patient support and device replacement management, said second application further allowing the user to view a list of therapeutic substance infusion devices implanted in one or more patients and schedule events pertaining to these devices;
a third computer readable remote program code device which allows a user access to literature and materials providing information concerning therapeutic substance infusion devices, said literature and materials being specifically targeted based upon user profile information;
and a fourth computer readable remote program code device that allows a clinician to communicate with a pharmacy wherein the clinician can place orders of a therapeutic agent on behalf of a patient.

41. The computerized system of claim 40, wherein the first computer readable remote program code device allows the user to provide feedback to the therapeutic substance infusion device manufacturer regarding the operation of the therapeutic substance infusion device.

42. The computerized system of claim 41, wherein the first computer readable remote program code device allows the user to view a therapeutic substance infusion device's capabilities and interconnectivities.

43. The computerized system of claim 42, wherein the second computer readable remote program code device allows the user to view at least one patient's prescription history and medical history.

44. The computerized system of claim 43, wherein the second computer readable remote program code device predicts a lifespan of at least one therapeutic substance infusion device.

45. The computerized system of claim 44, wherein the predicted lifespan is based on an algorithm provided by the therapeutic substance infusion device manufacturer.

46. The computerized system of claim 45, wherein the algorithm performs calculations for therapeutic substance infusion device replacement based on information learned by the therapeutic substance infusion device manufacturer on therapeutic substance infusion devices in an existing patient population.

47. The computerized system of claim 46, wherein the predicted lifespan includes a minimum life expectancy, a maximum life expectancy, and a predicted failure date for the at least one therapeutic substance infusion device.

48. The computerized system of claim 47, wherein the second computer readable remote program code device provides the user with a therapeutic substance infusion device replacement schedule to provide reminders of upcoming device replacement priorities.

49. The computerized system of claim 48, wherein a server file or a web page is accessed to provide access to the literature and materials concerning therapeutic substance infusion devices.

50. The computerized system of claim 49, wherein the fourth computer readable remote program code device allows the user to change prescription orders of a therapeutic agent on behalf of a patient.

51. The computerized system of claim 50, wherein the fourth computer readable remote program code device provides the user with an automated dosage calculator to provide predictive scenarios of contemplated treatment regimens.

52. The computerized system of claim 51, wherein the fourth computer readable remote program code device provides the user with at least one of pump refill reminders and prescription order reminders.

53. The computerized system of one of claims 52, wherein at least one computer readable remote program code device is implemented as an internet graphical user interface application portal.

54. The computerized system of claim 53, wherein the graphical user interface is a user-configurable template.

55. The computerized system of claim 54, wherein the server hosts a first computer readable server program code device for the entry of patient information into the database of patient information.

56. The computerized system of claim 55, wherein the server further hosts a second computer readable server program code device for the entry of therapeutic substance infusion device information into the database of therapeutic substance infusion device information.

57. The computerized system of claim 56, wherein the server further hosts a third computer readable server program code device for the entry of user profile information into the database of user profiles.

58. The computerized system of claim 57, wherein the server further hosts a fourth computer readable server program code device for the entry of therapeutic agent data into the database of therapeutic agent information.

59. The computerized system of claim 58, wherein the server hosts a fifth computer readable server program code device for the accessing and analysis of therapeutic agent data as applied to at least one specific patient.

60. The computerized system of claim 59, wherein the fifth computer readable server program code device determines compatibility with at least one therapeutic substance infusion device.

61. The computerized system of claim 60, wherein the therapeutic agent data comprises recommended dosages and agent interaction data.

62. The computerized system of claim 61, wherein the patient information further comprises therapeutic agent allergies for at least one specific patient.

63. The computerized system of claim 62, wherein the fifth computer readable server program code device provides therapeutic agent refill and order reminders.

64. The computerized system of claim 63, wherein access to the server is provided to third party users over a secure virtual connection over a public internetwork.

65. The computerized system of claim 64, wherein the third party users includes at least one of a pharmacist, a physician, a patient, and the therapeutic substance infusion device manufacturer.

66. The computerized system of claim 65, wherein the access to the server is provided following encrypted knowledge-based authentication.

67. The computerized system of claim 66, wherein the access to the server is provided following receipt of a passphrase over an encrypted channel.

68. The computerized system of claim 67, wherein access to the server is provided over a secure socket layer protocol connection.

69. The computerized system of claim 68, wherein the therapeutic substance infusion device manufacturer administers the server.

70. The computerized system of claim 69, wherein the connection of the server to the internetwork is a business-to-business connection with at least one therapeutic agent dispensary.

71. The computerized system of claim 70, wherein the connection of the server to the internetwork is a business-to-customer connection with at least one physician.

72. The computerized system of claim 71, wherein the connection of the server to the internetwork is a business-to-customer connection with at least one patient.

73. A computerized system providing for the management and configuration of one or more therapeutic substance infusion devices, comprising:
a network;
a database of patient information connected to said network;
a database of therapeutic substance infusion device information connected to said network;
a database of therapeutic agent information connected to said network;
a database of user profile information connected to said network;
a server connected to said network, wherein
  said server hosts a first computer readable server program code device for the entry of patient information into the database of patient information,
  said server hosts a second computer readable server program code device for the entry of therapeutic substance infusion device information into the database of therapeutic substance infusion device information, said server hosts a third computer readable server program code device for the entry of user profile information into the database of user profiles, and
  said server hosts a fourth computer readable server program code device for the entry of therapeutic agent data into the database of therapeutic agent information;
a suite of computer readable remote program code devices in communication with said server for support of said therapeutic substance infusion devices connected through said network including:
a first computer readable remote program code device adapted to allow a user to manage therapeutic substance infusion devices, said first computer readable remote program code device adapted to allow the user to submit therapeutic substance infusion device performance data to, and register a therapeutic substance infusion device with, a medical device manufacturer so that the medical device manufacturer can inform users of important therapeutic substance infusion device issues;
a second computer readable remote program code device that allows the user access to reports detailing therapeutic substance infusion device patient support and device replacement management, said report providing a list of therapeutic substance infusion devices implanted in one or more patients, a schedule of events pertaining to these devices, and an estimated lifetime of the therapeutic substance infusion device;
a third computer readable remote program code device which allows a user access to literature and materials providing information concerning therapeutic substance infusion devices, said literature and materials being specifically targeted based upon user profile information;
and a fourth computer readable remote program code device that allows a clinician access to a pharmacy wherein the clinician can place orders for a therapeutic agent on behalf of a patient.

* * * * *

UNITED STATES PATENT AND TRADEMARK OFFICE
CERTIFICATE OF CORRECTION

PATENT NO.      : 7,324,949 B2
APPLICATION NO. : 10/025023
DATED           : January 29, 2008
INVENTOR(S)     : Guy Scott Bristol Page 1 of 1

It is certified that error appears in the above-identified patent and that said Letters Patent is hereby corrected as shown below:

Col. 22, Line 53, Claim 23: "sewer" should be deleted - should read --server--

Col. 25, Line 3, Claim 53: "internet" should be deleted - should read --Internet--

Signed and Sealed this

Tenth Day of June, 2008

JON W. DUDAS
*Director of the United States Patent and Trademark Office*